United States Patent [19]

Rimbault et al.

[11] Patent Number: 4,665,202
[45] Date of Patent: May 12, 1987

[54] FLAVENE AND THIOFLAVENE DERIVATIVES

[75] Inventors: Christian G. Rimbault, Grand-Lancy; Philippe M. Narbel, Prangins, both of Switzerland

[73] Assignee: Zyma SA, Nyon, Switzerland

[21] Appl. No.: 644,006

[22] Filed: Aug. 24, 1984

[30] Foreign Application Priority Data

Aug. 31, 1983 [GB] United Kingdom ............... 8323293

[51] Int. Cl.$^4$ ............... C07D 405/04; C07D 309/34; C07D 335/06
[52] U.S. Cl. ............... 549/402; 544/62; 544/145; 544/151; 546/196; 546/202; 549/23; 549/398; 549/400; 549/403; 549/404; 549/406
[58] Field of Search ............... 544/62, 145, 151; 546/196, 202; 549/23, 398, 400, 402, 403, 404, 406; 514/222, 227, 320, 321, 432, 456, 459, 460

[56] References Cited

U.S. PATENT DOCUMENTS 3,567,605 3/1971 Becker ............... 549/400
3,796,727 3/1974 Debder ............... 549/400

FOREIGN PATENT DOCUMENTS 0025599 3/1981 European Pat. Off. ............ 549/400
357755 8/1922 Fed. Rep. of Germany ....... 549/406
1518003 1/1969 Fed. Rep. of Germany ....... 549/400

OTHER PUBLICATIONS

Rene, et al., Eur. J. Med. Chem–Chimica Therapeutica, Jan.–Feb. 1975, vol. 10, No. 1, pp. 72–78.
Fatome, et al., Eur. J. Med. Chem.–Chimica Therapeutica Jan.–Feb. 1976, vol. 11, pp. 81–82.
Bird, et al., J. Chem. Soc. 1, 1983, pp. 1831–1846.
CA 97: 98046v: Extractive Concentration of Ultramicro Quantity of Tungsten in Water.
Sartori, et al., J. Org. Chem., vol. 44, No. 5, 1979, pp. 803–805.
Oluwadiya, et al., J. Chem. Soc., 1978, pp. 88–92.
Olenovich, et al., Zhurnal Analiticheskoi Khimii, vol. 32, No. 12, pp. 2346–2351.
Ostensen, et al., Acta Chemica Scandinavica B31 (1977), 496–500.
Ostensen, et al., Acta Chemica Scandinavica B30 (1976), 635–639.
Badran, et al., J. Chem. Soc. 1976, pp. 1389–1392.
Mishrikey, et al., Acta Chemica Scandinaavica B30 (1976), 329–335.
Ostensen, et al., Acta Chemica Scandinavica B29 (1975), 1067–1070, 1075–1078.
Cullen, et al., J. Chem. Soc. 1975, pp. 1671–1674.
Bennett, et al., J. Chem. Soc. 1973, pp. 688–691.
Olaniyi, et al., J. Chem. Soc. 1973, pp. 179–184.
Bradomante, et al., J. Chem. Soc. 1973, pp. 163–166.
Cullen, et al., J. Chem. Soc. 1971, pp. 2848–2855.
Poluéktov, et al., Zhunal Analiticheskoi Khimii, vol. 25, No. 5, pp. 899–903, May 1970.
Cotterill, et al., J. Chem. Soc. 1970, pp. 1758–1764.
Nazarenko, et al., Chemistry of Reactions Between Ions of Multivitamins Elements and Organic Reagents, pp. 620–626.
Nazarenko, et al., The Chemistry of the Reactions Between Multivitamin Element Ions And Organic Reagents, pp. 1460–1463.
Weinges, et al., Liebigs Ann. Chem., vol. 711, pp. 184–204, (1968).
Weiges, et al., Chem. Ber., vol. 103, pp. 2344–2349, (1970).
Weinges, CA 79: 42289n (1973).
Girardin, et al., CA 83: 28053g, (1975).

Primary Examiner—Henry R. Jiles
Assistant Examiner—J. G. Mullins
Attorney, Agent, or Firm—Michael W. Glynn; Irving M. Fishman

[57] ABSTRACT

The invention relates to pharmaceutical preparations containing compounds of formula I

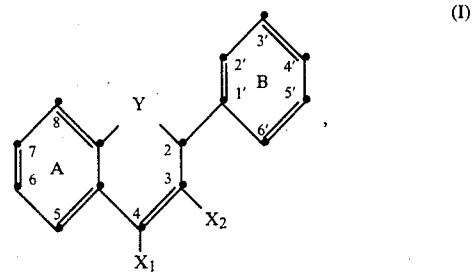

in which $X_1$ and $X_2$, independently of each other, represent hydrogen, halogen, unsubstituted or substituted amino or a quaternary ammonium salt; etherified or esterified hydroxy; free, etherified, esterified or oxidized mercapto; nitro; functionally modified formyl; free or functionally modified carboxyl; acyl; an unsubstituted or substituted hydrocarbon radical, or an unsubstituted or substituted heterocyclic radical; with the proviso that at least one of the radicals $X_1$ and $X_2$ is bonded by a carbon atom to the ring system and with the proviso that $X_1$ and $X_2$ cannot be together halogen and formyl; in which Y represents oxygen, sulfur, sulfinyl or sulfonyl but must be sulfur, sulfinyl or sulfonyl, if $X_1$ is hydrogen and $X_2$ is formyl, and the rings A and B are each unsubstituted or substituted; or pharmaceutically acceptable salts of such compounds that contain a salt-forming group, and to novel compounds of formula I. The compounds are useful e.g. for the treatment of diseases of the respiratory tract and of liver diseases. The are prepared by methods known per se.

6 Claims, No Drawings

FLAVENE AND THIOFLAVENE DERIVATIVES

The invention relates to pharmaceutical preparations containing flavenes, thioflavenes or oxidized derivatives thereof, especially 3-substituted, 4-substituted or 3,4-disubstituted flav-3-enes or thio-, sulfinyl- or sulfonylflav-3-enes, the therapeutic use of these compounds, novel compounds of this kind and processes for their manufacture. These compounds have valuable pharmaceutical properties.

The invention relates in particular to pharmaceutical preparations containing compounds of formula I

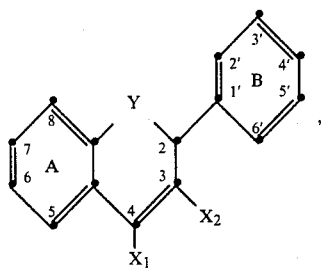

(I)

in which $X_1$ and $X_2$, independently of each other, represent hydrogen, halogen, unsubstituted or substituted amino or a quaternary ammonium salt; etherified or esterified hydroxy; free, etherified, esterified or oxidized mercapto; nitro; functionally modified formyl; free or functionally modified carboxyl; acyl; an unsubstituted or substituted hydrocarbon radicals, or an unsubstituted or substituted system heterocyclic radical; with the proviso that at least one of the radicals $X_1$ and $X_2$ is bonded by a carbon atom to the ring system and with the proviso that $X_1$ and $X_2$ cannot be together halogen and formyl; in which Y represents oxygen, sulfur, sulfinyl or sulfonyl but must be sulfur, sulfinyl or sulfonyl, if $X_1$ is hydrogen and $X_2$ is formyl; and the rings A and B are each unsubstituted or substituted; or pharmaceutically acceptable salts of such compounds that contain a salt-forming group.

In case Y is sulfinyl the corresponding sulfoxide compound may exist in its α- or in its β-form.

Unless otherwise noted, "lower" radicals are in particular those having up to 7, especially up to 4, carbon atoms. The term "substituted" in connection with organic groups or radicals always comprises preferably mono- or di- but also polysubstitution. A substituted ring A or B as mentioned before represents a benzene ring substituted e.g. by 1, 2, 3 or 4 substituents.

An unsubstituted or substituted amino group can be a primary, secondary or tertiary amino group. In the two last-mentioned amino groups, the nitrogen atom can carry as substituents unsubstituted or substituted aliphatic, cycloaliphatic, cycloaliphatic-aliphatic, aromatic, araliphatic, heterocyclic or heterocyclic-aliphatic hydrocarbon radicals, or acyl. Two substituents taken together can however also be an unsubstituted or substituted bivalent aliphatic hydrocarbon radical, for example lower alkylene, lower alkenylene or lower alkadienylene, in all of which the carbon atoms of the chain are optionally replaced by 1 or 2, preferably 1, heteroatoms selected from the group comprising e.g. oxygen, sulfur or unsubstituted or substituted nitrogen.

Secondary amino groups are in particular: lower-alkylamino, such as methylamino, ethylamino, n-propylamino, iso-propylamino, or di-n-butylamino; cycloalkylamino, e.g. cyclohexylamino, phenyl-lower-alkylamino, e.g. benzylamino; phenylamino; heterocyclylamino, e.g. 2-imidazolylamino; or heterocyclyl-lower-alkylamino, e.g. 2-imidazolylmethylamino, or acylamino.

Tertiary amino groups are in particular: di-lower alkylamino, such as dimethylamino, diethylamino, di-n-propylamino or di-isopropylamino; N-cycloalkyl-N-lower-alkylamino, e.g. N-cyclopentyl-N-methylamino; N-phenyl-N-lower-alkylamino, e.g. N-methyl-N-phenylamino; or N-phenyl-lower-alkyl-N-lower-alkylamino, e.g. N-benzyl-N-methylamino; lower alkyleneamino, aza-, oxa- or thia-lower alkyleneamino, lower alkenyleneamino, lower alkadienyleneamino; or di-acylamino.

Lower alkylamino and di-lower alkylamino groups may optionally be substituted within the lower alkyl portions, preferably by hydroxy and/or free or esterified carboxyl. Advantageously a hydroxy substituent is separated from the amino nitrogen atom by at least 2, preferably 2 or 3, carbon atoms. Such groups are for example: 2-hydroxyethylamino, N-(2-hydroxyethyl)-N-methylamino or di-(2-hydroxyethyl)-amino. Free or esterified carboxyl-substituted lower alkylamino is e.g. (N-carboxymethyl)amino or (N-methoxycarbonylmethyl)amino.

Lower-alkyleneamino having 3 to 8, preferably 5 to 7, ring members is for example: pyrrolidino, 2,5-dimethyl-pyrrolidino, piperidino, 2-methyl-piperidino, 3-ethyl-piperidino, hexahydro-1H-azepino or octahydroazocino. Mentioned as aza-, oxa- or thia-lower alkyleneamino having 6 to 8, preferably 6, ring members, in which an aza-nitrogen atom is unsubstituted or preferably substituted for example lower alkyl, hydroxy-($C_2$–$C_7$)-alkyl, phenyl, phenyl-lower-alkyl or pyridyl or acyl, and wherein the hetero atom is separated at least by 2 carbon atoms from the amino-nitrogen atom, are for example piperazino, 4-methylpiperazino, 4-(2-hydroxyethyl)-piperazino or 4-acetylpiperazino, further e.g. morpholino or thiomorpholino.

Lower alkenyleneamino has preferably 5 to 7 ring members and is characterised in that the amino nitrogen is not bonded directly to the double bond, such as 2,5-dihydro-1H-pyrrol-1-yl or 1,2,3,6-tetrahydro-1-pyridyl.

Lower alkadienyleneamino is e.g. a six-membered ring, e.g. 1,4-dihydro-1-pyridyl, or preferably a five-membered ring which is of aromatic character, e.g. 1H-pyrrol-1-yl. One or two of the carbon atoms may be replaced by e.g. nitrogen thus resulting in e.g. 1H-triazol-1-yl, 1H-pyrazol-1-yl or preferably 1H-imidazol-1-yl radicals which may be substituted by the substituents indicated below for heterocyclic radicals or are advantageously unsubstituted.

To be mentioned as secondary or also as tertiary amino groups in this connection are also amino groups substituted by arylamino or arylimino groups, for example phenylhydrazino or phenylazo, or lower alkylamino or lower alkylimino groups, for example methylhydrazino or methylazo.

Acylamino is preferably lower-alkanoylamino, such as acetylamino, benzoylamino or phenyl-lower-alkanoylamino, both of which can be substituted in the phenyl ring for example with halogen, nitro, lower alkyl and/or lower alkoxy.

Di-acylamino is e.g. di-lower alkanoylamino, such as diacetylamino, or dibenzoylamino which optionally is substituted in the phenyl rings e.g. by halogen, lower alkyl, lower alkoxy and/or nitro.

Quaternary ammonium salts are derived from corresponding tertiary amino groups mentioned above, contain as quaternary substituent optionally substituted lower alkyl, for example lower alkyl, hydroxy- or halo-lower alkyl, phenyl-lower alkyl, phenoxy-lower alkyl or phenylthio-lower alkyl, wherein the phenyl moiety can in each case be unsubstituted or substituted by e.g. lower alkyl, lower alkoxy, halogen, trifluoromethyl and/or by nitro, and are preferably a tri-lower-alkylammonium salt, but also e.g. a phenyl-lower-alkyl-di-lower-alkylammonium salt or a phenoxy-lower-alkyl-di-lower-alkylammonium salt. They correspond to the salts defined hereinafter, especially the salts mentioned in particular as being pharmaceutically acceptable, non-toxic acid addition salts, and more especially those salts formed with hydrohalic acids, sulphuric or phosphoric acids.

Halogen is e.g. bromo or iodo, preferably fluoro and especially chloro.

Etherified hydroxy is in particular lower alkoxy or lower alkoxy substituted by e.g. halogen, hydroxy, amino, mono- or di-lower-alkylamino, epoxy or preferably by free or esterified carboxyl, e.g. (O-carboxymethyl)oxy or (O-ethoxycarbonylmethyl)oxy; further lower alkenyloxy, cycloalkyloxy, phenyloxy, phenyl-lower-alkoxy, heterocyclyloxy or heterocyclyl-lower alkoxy, such as pyridyl-oxy or -methoxy, furyloxy or -methoxy or thienyl-oxy or -methoxy.

Esterified hydroxy is preferably alkanoyloxy, especially lower alkanoyloxy, or benzoyloxy that optionally is substituted by hydroxy, lower alkoxy, halogen, lower alkyl and/or nitro; but can also be e.g. lower alkoxycarbonyloxy or N-lower alkylthiocarbamoyloxy.

Etherified mercapto is in particular unsubstituted or substituted lower-alkylthio, preferably by free or esterified carboxyl, e.g. (S-carboxymethyl)-thio or (S-ethoxycarbonylmethyl)-thio, but also e.g. by halogen, e.g. trifluoromethylthio, hydroxy, amino, mono- or di-lower-alkylamino or epoxy; phenylthio or phenyl-lower-alkylthio, heterocyclylthio or heterocyclyl-lower alkylthio, e.g. 2-imidazolylthio, 2"H-3"-formyl-2"-phenyl-1"-benzopyran-4"-yl-thio or 2-imidazolylmethylthio.

Esterified mercapto is preferably lower alkylsulfonyloxy, e.g. methylsulfonyloxy, or optionally substituted phenylsulfonyloxy, but can also be e.g. lower alkanoylthio, thiocyanato or benzoylthio which is optionally substituted in the phenyl ring as described below.

Oxidized mercapto is for example phenylsulfinyl, phenyl-lower alkylsulfinyl, lower alkylsulfinyl, phenylsulfonyl, phenyl-lower alkylsulfonyl or lower alkylsulfonyl, wherein phenyl radicals can be unsubstituted or be substituted as described below.

Free or functionally modified carboxyl is for example carboxy, esterified carboxyl, especially lower-alkoxycarbonyl, such as methoxycarbonyl or ethoxycarbonyl; amidated carboxy, particularly carbamoyl which is free or mono- or disubstituted by lower alkyl, by di-lower-alkylamino-alkyl or by phenyl which is unsubstituted or for its part substituted e.g. by halogen, lower alkyl and/or lower alkoxy; and also the cyano group.

The acyl radicals of an aliphatic carboxylic acid are in particular acyl radicals of alkanecarboxylic acids, i.e. alkanoyl, especially lower-alkane-carboxylic acids or lower-alkanedicarboxylic acids, i.e. lower alkanoyl or carboxy-substituted lower alkanoyl, but also of lower-alkenecarboxylic acids or lower-alkenedicarboxylic acids, i.e. lower alkenoyl or carboxy-substituted lower alkenoyl, and also of substituted lower-alkanecarboxylic acids, for example substituted by halogen, i.e. halo-lower alkanoyl, such as trifluoroacetyl.

The acyl radicals of cycloaliphatic, cycloaliphatic-aliphatic, aromatic, aromatic-aliphatic carboxylic acids have, both for the ring and for the optionally present aliphatic part, the below-given meaning of the corresponding hydrocarbon radicals and are preferably cycloalkanoyl, benzoyl or phenyl-lower alkanoyl. They can also carry substituents, for example, hydroxy, halogen, lower alkyl and/or lower alkoxy.

An unsubstituted or substituted hydrocarbon radical is for example: an aliphatic, cycloaliphatic, cycloaliphatic-aliphatic, aromatic, aromatic-aliphatic, or heterocyclic-aliphatic radical.

An aliphatic hydrocarbon radical, which is unsubstituted or substituted, is especially alkyl and in particular lower alkyl, but may be also alkenyl or alkynyl, especially lower-alkenyl or lower-alkynyl.

Substituents of aliphatic hydrocarbon radicals are for example: free, esterified or etherified hydroxy, free or etherified mercapto, lower-alkylthio, lower alkylsulfinyl, halogen or nitro, also free or esterified carboxyl, cyano and/or formyl.

Lower alkyl is preferably methyl, but may be also e.g. ethyl, n-propyl, isopropyl, n-butyl, isobutyl, sec-butyl, tert-butyl, n-pentyl, isopentyl, neopentyl, n-hexyl, isohexyl or n-heptyl. Lower alkyl can also be substituted for example by nitro, hydroxy, halogen, especially fluoro, hydroxycyano, hydroxyamino, lower alkylthio, acyl, for example lower alkanoyl, such as acetylmethyl, or by free or esterified carboxy, preferably lower-alkoxycarbonyl, for example methoxycarbonylethyl; unsubstituted or substituted imino, such as free or esterified hydroxyimino, lower-alkylimino or unsubstituted or substituted phenylimino; acyloxyimino, e.g. acetyloxyiminomethyl, di-lower-alkylimmonio-lower-alkyl, e.g. dimethylimmoniomethyl, amino, mono- or di-lower-alkylamino or lower-alkyleneamino, for example pyrrolidino or piperidino. A further possible substituted lower alkyl group is the lower alkyl group substituted by a 2,2-di-lower-alkyl-4,6-dioxo-1,3-dioxan-5-ylidene group, such as (2,2-dimethyl-4,6-dioxo-1,3-dioxan-5-ylidene)-methyl.

Lower alkenyl is for example: vinyl, allyl, 1-propenyl, isopropenyl, 1- or 2-methallyl or 2- or 3-butenyl. Lower alkynyl is for example: propargyl or 2-butynyl. Lower alkenyl may be substituted by e.g. free or esterified carboxy, nitro, lower alkylsulfinyl, lower alkylsulfonyl, aryl or lower alkylthio. Lower alkynyl may be substituted by e.g. aryl or free or esterified carboxy.

An unsubstituted or substituted cycloaliphatic or cycloaliphatic-aliphatic radical is for example mono-, bi- or polycyclic cycloalkyl, cycloalkenyl or cycloalkyl-lower alkyl, cycloalkenyl-lower-alkyl, cycloalkyl-lower-alkenyl or cycloalkenyl-lower alkenyl, wherein the cycloalkyl radical contains up to 12, for example 3-8, particularly however 3-6, ring carbon atoms, whilst a cycloalkenyl radical has for example up to 12, preferably however 5-6, carbon atoms and one or two double bonds. The aliphatic part of a cycloaliphatic-aliphatic radical can contain up to 7, but preferably up to 4, carbon atoms. The stated cyclic radicals can be, if desired, mono-, di- or polysubstituted, in a manner analogous to that in the case of the aromatic radicals given below.

An unsubstituted or substituted aromatic hydrocarbon radical, i.e. aryl, is for example a monocyclic, bicyclic or polycyclic aromatic radical, such as the phenyl or naphthyl radical, which may optionally be substituted as described below for the rings A and B. An unsubstituted or substituted aromatic-aliphatic hydrocarbon is for example an aliphatic hydrocarbon radical carrying up to 3 mono-, bi- or polycyclic aromatic radicals, which may also be substituted. It is in particular phenyl-lower-alkyl, but also phenyl-lower-alkenyl or phenyl-lower-alkynyl. These radicals can, if desired, be mono-, di- or polysubstituted in the aromatic part as described below for the rings A and B and also in the aliphatic part as described above for aliphatic hydrocarbon radicals.

A heterocyclic radical as such or in a heterocyclic-aliphatic group, as well as "heterocyclyl" when referred to above or hereinafter in connection with organic groups or radicals, e.g. within expressions like heterocyclyloxy, heterocyclyl-lower alkoxy, heterocyclylthio, heterocyclyl-lower alkylthio, heterocyclylamino or heterocyclyl-lower alkylamino, is e.g. a monocyclic heterocyclic radical having 3 to 8, preferably 5 to 8 and advantageously 5 or 6 ring members, which is preferably bonded by a ring carbon atom to the moiety that it is joined with. A heterocyclic radical as a value of X is always bonded by a carbon atom to the 3-methylidene substituent of the flavanone moiety. It contains e.g. 0 to 4, preferably 1, 2 or 3 double bonds and is advantageously of aromatic character; in the latter case it is named "heteroaryl".

Usually "heterocyclyl" contains 1 to 4, identical or different, hetero atoms as ring members, especially nitrogen, oxygen and/or sulfur atoms. Preferred are aza-, oxa-, thia-, thiaza-, thiadiaza-, oxaza-, oxadiaza-, diaza-, triaza- or tetraza-monocycles. Monocyclic "heterocyclyl" may optionally contain e.g. 1 or 2, preferably 1, fused benzo rings.

Monocyclic five-membered heteroaryl is e.g. pyrryl, pyrazolyl, imidazolyl, triazolyl, tetrazolyl, furyl, thienyl, isoxazolyl, oxazolyl, oxadiazolyl, isothiazolyl, thiazolyl, or thiadiazolyl, while monocyclic six-membered heteroaryl is e.g. pyridyl, pyridazinyl, pyrimidinyl, pyrazinyl or triazinyl. Monocyclic heteroaryl fused with one benzo ring is e.g. indolyl, isoindolyl, benzimidazolyl, benzofuranyl, benzothienyl, benzothiazolyl, benzoxazolyl, quinolinyl or benzopyranyl. Monocyclic five or six-membered heterocyclyl being not of aromatic character is preferably the partially saturated corresponding heteroaryl, e.g. dihydropyrryl, such as 4,5-dihydro-3-pyrrolyl, dihydrooxazolyl, such as 4,5-dihydro-2-oxazolyl, or 1,2-dihydropyrimidinyl, such as 1,2-dihydro-4-pyrimidinyl or tetrahydro-triazinyl, such as tetrahydro-1,2,4-triazin-3-yl.

Heterocyclyl radicals are unsubstituted or may be substituted, such as mono- or poly-substituted, such as, especially, disubstituted by hydroxy, lower alkoxy, lower alkanoyloxy, halogen, mercapto, lower alkylthio, phenylthio, lower alkyl, hydroxy-lower alkyl, lower alkoxy-lower alkyl, carboxy-lower alkyl, optionally N-lower alkylated amino-lower alkyl, amino, lower alkylamino, di-lower alkylamino, lower alkyleneamino, aza-, oxa- or thia-lower alkyleneamino, or acylamino, such as lower alkanoylamino, carboxy, esterified carboxy, such as lower alkoxycarbonyl, optionally substituted carbamoyl, such as N-mono- or N,N-di-lower alkylated carbamoyl, cyano, sulfo or sulfamoyl; phenyl optionally substituted by lower alkyl, nitro, lower alkoxy and/or by halogen; cycloalkyl, nitro, oxo and/or oxido.

Phenyl radicals when referred to within expressions like phenyloxy, phenyl-lower alkoxy, phenylthio, phenyl-lower alkylthio, phenylamino, phenyl-lower alkylamino, benzoylthio, phenylsulfinyl, phenyl-lower alkylsulfinyl, phenylsulfonyl or phenyl-lower alkylsulfonyl are unsubstituted or may be substituted in exactly the same way as described above for heterocyclyl radicals, with the exception of oxo and oxido substituents which are not suitable in case of phenyl.

Functionally modified formyl is for example an acetal or semiacetal, such as di-lower-alkylacetal or a lower-alkyl-semiacetal, for example dimethylacetal, diethylacetal or ethylsemiacetal, an oxime or oxime ether, such as an oxime lower-alkylether, for example an oxime methylether or an oxime ethylether, unsubstituted or substituted imine, such as a lower-alkyl- or arylimine, for example a methyl-, ethyl- or phenylimine, unsubstituted or substituted hydrazone, such as a lower-alkyl- or aryl-substituted hydrazone, for example a methyl-, ethyl- or phenyl-substituted hydrazone, semicarbazone or thiosemicarbazone.

The rings A and B may optionally be substituted preferably by free, etherified or esterified hydroxy, such as hydroxy, lower alkoxy or lower alkanoyloxy; etherified mercapto, such as lower alkylthio; secondary or tertiary amino, such as lower alkylamino, di-lower alkylamino, lower alkyleneamino, aza-, oxa- or thia-lower alkyleneamino, or acylamino; lower alkyl; halogen; free or functionally modified carboxyl, such as carboxy, lower alkoxycarbonyl, carbamoyl, N-mono- or N,N-di-lower alkylcarbamoyl or cyano; nitro; or amidated sulfo, such as sulfamoyl, N-lower-alkyl, N,N-di-lower-alkyl- or N-phenylsulfamoyl. Further substituents that come into consideration are e.g. amino, di-acylamino or sulfo, or methylenedioxy.

If the lower alkyl part of the radicals lower alkoxycarbonyl, lower alkoxy, lower alkylthio, lower alkylamino, di-lower alkylamino, N-lower alkyl- or N,N-di-lower alkylcarbamoyl and similar ones is substituted by hydroxy, mercapto, amino or lower alkylamino, methyl is not intended as a value of lower alkyl due to lacking stability of those compounds.

Cycloalkyl is e.g. cyclohexyl or cyclopropyl.

Lower alkoxy is e.g. methoxy, ethoxy, n-propoxy, or isopropoxy, n-butoxy or tert.butoxy.

Lower alkylthio is for example methylthio, ethylthio, n-propylthio, isopropylthio, n-butylthio or tert-butylthio.

Lower alkenyloxy is for example vinyloxy or allyloxy.

Cycloalkyloxy is for example cyclopentyloxy, cyclohexyloxy, or also cyclopropyloxy or cycloheptyloxy.

Phenyl-lower alkoxy is for example benzyloxy, 2-phenylethoxy or diphenylmethoxy.

Phenyl-lower alkylthio is for example benzylthio or 2-phenylethylthio.

Lower alkoxycarbonyloxy is for example methoxycarbonyloxy or ethoxycarbonyloxy.

Lower alkylthiocarbamoyloxy is for example N-methylthiocarbamoyloxy.

Alkanoyloxy is e.g. palmitoyloxy; lower alkanoyloxy which is preferred represents formyloxy or lower alkylcarbonyloxy, e.g. acetoxy, propionyloxy, butyryloxy, isobutyryloxy, pivaloyloxy or valeroyloxy.

Lower alkanoylthio is for example formylthio, acetylthio, propionylthio, isobutyrylthio, pivaloylthio or valeroylthio.

Lower alkanoyl comprises formyl and lower alkylcarbonyl, e.g. acetyl, propionyl, n-butyryl, pivaloyl or valeroyl; alkanoyl is e.g. palmitoyl.

Carboxy-substituted lower alkanoyl is for example oxaloyl, malonoyl, succinoyl, glutaroyl or adipinoyl.

Lower alkenoyl is e.g. propenoyl (acryloyl), 2-butenoyl (crotonoyl) or 3-butenoyl.

Carboxy-substituted lower alkenoyl is e.g. maleinoyl or fumaroyl.

Cycloalkanoyl is preferably cyclo($C_3$–$C_8$)alkanoyl, such as cyclohexanoyl.

Lower alkylsulfinyl is for example methylsulfinyl, ethylsulfinyl, n-propylsulfinyl, isopropylsulfinyl, n-butylsulfinyl, isobutylsulfinyl or tert-butylsulfinyl.

Lower alkylsulfonyl is for example methylsulfonyl, ethylsulfonyl, n-propylsulfonyl, isopropylsulfonyl, n-butylsulfonyl, isobutylsulfonyl or tert-butylsulfonyl.

Phenylsulfonyloxy is optionally substituted in the phenyl part in a manner analogous to that in the case of the aromatic radicals given above, and is preferably phenylsulfonyloxy or p-toluenesulfonyloxy.

Phenyl-lower alkylsulfinyl is for example benzylsulfinyl or 2-phenylethylsulfinyl.

Phenyl-lower alkylsulfonyl is for example benzylsulfonyl or 2-phenylethylsulfonyl.

The compounds of the formula I possess valuable pharmacological properties. They, for example, stimulate the mucociliary transport in bronchia, and they modify the secretion of the viscoelasticity of mucus produced by bronchial and tracheal glands. These properties make the compounds useful for the treatment of diseases of the respiratory tract, as for example, chronic bronchitis, in mammals.

The stimulation of mucociliary transport can be demonstrated with pharmacological model of frog oesophagus. In this system, the speed of transport of particles by the ciliated epithelium of frog oesophagus is measured according to Puchelle et al. [Bull. Physio. path. resp. 12, 771–779 (1976)].

By adding solutions of compounds to be tested on the frog oesophagus an increase in the speed of transport is measured. This effect appears when using solutions of compounds of formula I with a concentration of only $10^{-3}$–$10^{-4}$M or less.

The relaxing effect of these compounds on the smooth muscles of bronchi can be demonstrated by the protection afforded by these compounds against the broncho-spasm induced by histamine aerosol in Guinea-pigs. Pretreatment of Guinea-pigs by i.p. route with compounds of formula I at a dose of 100 mg/kg or less allows the animals to resist more than 5 minutes to the histamine aerosol; control animals do not resist more than 1 minute and 30 sec.

The modification of viscoelasticity of mucus samples caused by compounds of formula I can be measured with a microrheometer according to C. Marriott [Advances in experimental Medicine and Biology, 144, 75–84 (1981)].

The mucus is obtained from fresh pig's stomach scrapings and is purified biochemically before use. The test compounds are dissolved in specific solvents, distilled water, phosphate buffer, methanol aqueous mixture, or in DMSO (dimethylsulfoxide), 50 mg aliquotes of mucus with 5–10 µl of the test solution are added. The samples are mixed, centrifused and incubated for 30 min. for interaction to take place. The samples are then loaded into the cell of an oscillating sphere magnetic microrheometer and a 200 µm iron sphere is placed centerally in the sample which is allowed 5 minutes for relaxation to take place. The rheological behaviour is evaluated at 25° C. over the frequency range of 0.1 to 20 Hz. The elastic modulus G' of mucus is changed, preferably reduced, but also enlarged, by using the compounds of formula I.

The mucroregulators properties of the compounds of formula I can be evaluated by the use of the "Ussing Chamber method" described in Respirat. Environ. Exercise Physiol. 49, 1027–1031 (1980).

In this method pieces of pig trachea are kept alive in physiological saline medium. The outlets of tracheal glands are observed via a light microscope. The mucus output is triggered either by electric stimulation or by addition of pilocarpine to the incubation medium. The number and the surface of mucus hillocks are recorded via a video tape recorder. The addition of the compounds of formula I in the incubation medium at a concentration of only $10^{-4}$M or less modifies the number and the surface of hillocks reflecting a change in mucus secretion.

The compound of formula I also have properties of preventing the hepatic necrosis and of immunomodulation.

The hepatic antinecrotic properties of these substances can be demonstated by the galactosamine hepatitis test in the rat and the carbon-tetrachloride hepatitis test in the mouse. The galactosamine hepatitis in the rat is a well-known model to faithfully reproduce the morphological and biochemical changes of the human viral heptatis [K. Decker et al., Adv. enzyme regul. 11, 205 (1973)].

Rats treated intraperitoneally or orally with doses of the compounds of formula I varying from 10 to 200 mg/kg are protected from the hepatic necrosis induced with glacatosamine or carbonetetrachloride. The heptatic effect is assessed by dosage of plasma transaminases and by measuring the sleeping time induced by pentobarbital which reflects liver function.

The immunomodulation properties of these substances can be demonstrated by a battery of tests classically used in immunology:

(a) humoral immunity test: production of antibodies against the bovine albumine in the mouse. Compounds of formula I, administered at a dose of 10 to 100 mg/kg, 15 minutes after the antigen (bovine albumine), stimulate the antibody production against this antigen, as measured 15 to 28 days later by the passive hemagglutination technique.

(b) cellular immunity test: delayed hypersensitivity reaction to sheep red blood cells in mice. Compounds of formula I administered at a dose of 10 to 100 mg/kg by subcutaneous route at the same time as the antigen stimulate the delayed hypersensitivity reaction triggered off 21 days later by a subcutaneous injection of the antigen.

(c) cytotoxicity test of mice macrophages against tumoral cells. The macrophages collected from mice having been treated by doses of 10 to 100 mg/kg of compounds of formula I, have a stimulated cytotoxicity against tumoral target cells.

These tests establish that the three main processes involved in the immunological defence (humoral immunity, cellular immunity and macrophages) are modified by the action of the compounds of formula I and demonstrate their immunomodulating properties.

These various properties particularly designate the compounds of formula I for the treatment in mammals of acute and chronic diseases induced by viruses, toxins or alcohol. As a matter of fact, during these diseases, the impairment of the hepatic functions results essentially from the hepatic necrosis. This alterations can be diminished by the new substances.

The stimulation of the immunologic defences induced by these substances is useful for the treatment in mammals of the acute and chronic viral hepatitis and also for the treatment of all cases when there is an alteration of immunologic defence reactions such as repeating bacterial or viral infections or carcinogenous diseases. In the latter case, the interest of the substances is specifically demonstrated by the activation of cytotoxic effect of macrophages for tumoral cells.

Compounds of formula I are also able to diminish an increased microvacular permeability and therefore are very potent antioedamators agents in mammals.

Increased microvascular permeability with generalized oedema can be induced in rats by administration of galactosamine and dextran.

At doses administrated parenterally or orally varying from 10 to 500 mg/kg compounds of formula I prove to be able to reduce the oedema as measured by the reduction in the accumulation of $I_{125}$ labelled albumine in paws of animals which receive previously an i.v. injection of $I^{125}$ albumine. This measurement is an estimation of the micro-vascular permeability as reported by O. P. Gulati et al., Archives Int. de Pharmacodynamie et de Thérapie 263, pp. 272-287 (1983).

The invention relates especially to pharmaceutical preparations containing compounds of formula I, in which $X_1$ and $X_2$ independently of each other, represent hydrogen, halogen, primary, secondary or tertiary amino, acrylamino, di-acylamino or a quarternary ammonium salt; unsubstituted or substituted lower-alkoxy, lower-alkenyloxy, cycloalkoxy, phenyloxy, phenyl-lower-alkoxy, heterocyclyloxy or heterocyclyl-lower alkoxy, lower-alkoxycarbonyloxy, lower alkylsulfonyloxy, phenylsulfonyloxy, formyloxy, lower-alkylcarbonyloxy or benzoyloxy; mercapto, unsubstituted or substituted lower-alkylthio, phenylthio, phenyl-lower-alkylthio, heterocyclythio or heterocyclyl-lower alkylthio; lower-alkoxy-carbonylthio or lower-alkanoylthio; unsubstituted or substituted phenylsulfinyl, phenyl-lower-alkysulfinyl, lower alkylsulfinyl, phenylsulfonyl, phenyl-lower-alkylsulfonyl or lower alkylsulfonyl; nitro; formyl, acetalised or semiacetalised formyl, or unsubstituted or substituted imino; free or esterified carboxyl, amidated carboxyl or cyano; unsubstituted or substituted lower alkylcarbonyl, cycloalkanoyl, benzoyl or phenyl-lower alkylcarbonyl; or a saturated or unsaturated, unsubstituted or substituted aliphatic, cycloaliphatic, cycloaliphatic-aliphatic, aromatic, aromatic-aliphatic, heterocyclic or heterocyclic-aliphatic radical; with the proviso that at least one of the radicals $X_1$ and $X_2$ is bonded by a carbon atom to the ring system and with the further proviso that $X_1$ and $X_2$ cannot be together halogen and formyl; Y represents oxygen, sulfur, sulfinyl or sulfonyl but must be sulfur, sulfinyl or sulfonyl, if $X_1$ is hydrogen and $X_2$ is formyl; and the rings A and B are each unsubstituted or substituted by 1, 2, 3 or 4 substitutents; or pharmaceutically acceptable salts of such compounds that contain a salt-forming group.

The invention relates more specifically to pharmaceutical preparations containing compounds of formula I, in which one of the radicals $X_1$ and $X_2$ is hydrogen, halogen, amino, unsubstituted or substituted lower-alkylamino, di-lower-alkylamino, cycloalkylamino, N-cycloalkyl-N-lower-alkylamino, phenylamino, N-phenyl-N-lower-alkylamino, phenyl-lower-alkylamino, N-phenyl-lower-alkyl-N-lower-alkylamino, lower alkyleneamino, aza-, oxa-, or thia-lower alkyleneamino, heterocyclylamino, heterocyclyl-lower alkylamino, lower-alkanoylamino, benzoylamino, phenyl-lower alkylcarbonylamino or phenylhydrazino; a tri-lower-alkylammonium salt; unsubstituted or substituted lower-alkoxy, lower-alkenyloxy, phenyloxy, phenyl-lower-alkoxy, heterocyclyloxy, heterocyclyl-lower alkoxy, lower alkoxycarbonyloxy, lower alkanoyloxy or benzoyloxy; mercapto, unsubstituted or substituted lower-alkylthio, phenylthio or phenyl-lower-alkylthio, heterocyclylthio or heterocyclyl-lower alkylthio; and wherein the other of the two radicals $X_1$ and $X_2$ represents formyl, formyl acetalised or semiacetalised by a lower alkanol, imino optionally substituted by hydroxy, lower alkoxy, lower alkyl, unsubstituted or substituted phenyl, or unsubstituted or substituted amino; carboxy, lower-alkoxycarbonyl, optionally N-lower-alkylated, N,N-di-lower-alkylated or N-phenylated carbamoyl, or cyano; unsubstituted or substituted lower alkylcarbonyl, benzoyl or phenyl-lower-alkylcarbonyl; or an unsubstituted or substituted alkyl, alkenyl or alkynyl radical, unsubstituted or substituted cycloalkyl, cycloalkenyl, cycloalkyl-lower alkyl, cycloalkenyl-lower-alkyl, cycloalkyl-lower-alkenyl or cycloalkenyl-lower-alkenyl, or unsubstituted or substituted phenyl or phenyl-lower-alkyl or unsubstituted or substituted heterocyclyl bonded by a carbon atom, or heterocyclyl-lower alkyl; wherein the term "heterocyclyl" is always defined as an aza-, thia-, oxa-, thiaza-, oxaza-, diaza-, triaza- or tetraza-monocycle of 3 to 8 ring members having from zero to four double bonds and optionally containing a fused benzo ring; with the proviso that $X_1$ and $X_2$ cannot be together halogen and formyl; Y represents oxygen, sulfur, sulfinyl or sulfonyl but must be sulfur, sulfinyl or sulfonyl, if $X_1$ is hydrogen and $X_2$ is formyl; and the rings A and B are each unsubstituted or substituted by 1, 2 or 3 substituents; or pharmaceutically acceptable salts of such compounds that contain a salt-forming group.

Preferred are pharmaceutical preparations containing compounds of formula I, wherein one of the radicals $X_1$ and $X_2$ is halogen, amino, a tri-lower-alkylammonium salt, lower alkoxycarbonyloxy or mercapto; or represents optionally substituted phenylamino, phenylhydrazino, benzoylamino, phenyloxy, benzoyloxy, phenylthio, N-phenyl-N-lower-alkylamino, phenyl-lower-alkylamino, N-phenyl-lower-alkyl-N-lower-alkylamino, phenyl-lower-alkylcarbonylamino, phenyl-lower-alkoxy or phenyl-lower-alkylthio, heterocyclylamino, heterocyclyl-lower alkylamino, heterocyclyloxy, heterocyclyl-lower alkoxy, heterocyclylthio, or heterocyclyl-lower alkylthio. in which radicals $X_1$ or $X_2$ respectively, the substituents optionally present are hydroxy, lower alkoxy, lower alkanoyloxy, lower alkylthio, amino, lower alkylamino, di-lower alkylamino, acylamino, di-acrylamino, lower alkyl, phenyl, halogen, formyl, carboxy, lower alkoxycarbonyl, carbamoyl, N-mono- or N,N-di-lower alkylcarbamoyl, cyano, nitro, sulfo, or sulfamoyl, N-lower alkyl-, N,N-di-lower alkyl- or N-phenylsulfamoyl; or wherein one of the radicals $X_1$ and $X_2$ is unsubstituted or substituted lower alkylamino, di-lower alkylamino, cycloalkylamino, N-cycloalkyl-N-lower alkylamino, lower alkyleneamino, aza-, oxa- or thia-lower alkyleneamino, lower alkanoylamino, lower alkoxy, lower alkenyloxy, lower alkanoyloxy or lower alkylthio, in which radicals $X_1$ or $X_2$ respectively, the substituents optionally present are hydroxy, lower alkoxy, lower alkanoyloxy, amino, lower alkylamino, di-lower alkylamino, acylamino, di-acrylamino, carboxy, lower alkoxycarbonyl, carbamoyl, N-mono- or N,N-di-lower-alkylcarbamoyl, cyano or phenyl that optionally is substituted by carboxy, lower alkoxycarbonyl or cyano; and wherein the other of the two radicals $X_1$ and $X_2$ represents formyl, formyl acetalised or semiacetalised by a lower alkanol, imino optionally substituted by hydroxy, lower alkoxy, lower alkyl or amino which may be optionally substituted for its part by lower alkyl, phenyl or carbamoyl; carboxy, lower-alkoxycarbonyl, carbamoyl, N-mono- or N,N-di-lower alkylcarbamoyl or cyano; or represents an unsubstituted or substituted alkyl, alkenyl or alkynyl radical, unsubstituted or substituted cycloalkyl, cycloalkenyl, cycloalkyl-lower-alkyl, cycloalkenyl-lower-alkyl, cycloalkyl-lower-alkenyl or cycloalkenyl-lower alkenyl or an unsubstituted or substituted phenyl or phenyl-lower-alkyl radical, unsubstituted or substituted phenylimino, N-phenylated carbamoyl, lower alkylcarbonyl, benzoyl or phenyl-lower alkylcarbonyl, or unsubstituted or substituted heterocyclyl bonded by a carbon atom, or heterocyclyl-lower alkyl, in which radicals $X_1$ or $X_2$ respectively, the substituents optionally present are hydroxy, lower alkoxy, lower alkanoyloxy, halogen, mercapto, lower alkylthio, carboxy, lower alkoxycarbonyl, carbamoyl, N-mono- or N,N-di-lower alkylcarbamoyl, cyano, nitro, amino, lower alkylamino, di-lower-alkylamino, acrylamino, diacrylamino, lower alkyleneamino, phenyl or lower alkyl; wherein the term "heterocyclyl" is always defined as an aza-, thia-, oxa-, thiaza-, oxaza-, diaza-, triaza- or tetraza-monocycle of 3 to 8 ring members having from zero to four double bonds and optionally containing a fused benzo ring; with the proviso that $X_1$ and $X_2$ cannot be together halogen and formyl; Y represents oxygen, sulfur, sulfinyl or sulfonyl; and the rings A and B are each unsubstituted or substituted by 1, 2 or 3 substituents selected from the group consisting of hydroxy, lower alkoxy, lower alkanoyloxy, lower alkylthio, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl, N-lower alkyl-, N,N-di-lower alkyl- or N-phenylsulfamoyl; or pharmaceutically acceptable salts of such compounds that contain a salt-forming group.

Further preferred are pharmaceutical preparations containing compounds of formula I, wherein one of the radicals $X_1$ and $X_2$ is hydrogen; and the other is formyl acetalised or semiacetalised by a lower alkanol, imino optionally substituted by hydroxy, lower alkoxy, lower alkyl or amino which may be optionally substituted for its part by lower alkyl, phenyl or carbamoyl; carboxy, lower-alkoxycarbonyl, carbamoyl, N-mono- or N,N-di-lower alkylcarbamoyl or cyano; or represents an unsubstituted or substituted alkyl, alkenyl or alkynyl radical, unsubstituted or substituted cycloalkyl, cycloalkenyl, cycloalkyl-lower-alkyl, cycloalkenyl-lower-alkyl, cycloalkyl-lower-alkenyl or cycloalkenyl-lower alkenyl, unsubstituted or substituted phenylimino, N-phenylated carbamoyl, lower alkylcarbonyl, benzoyl or phenyl-lower alkylcarbonyl, unsubstituted or substituted phenyl, phenyl-lower-alkyl, heterocyclyl bonded by a carbon atom, or heterocyclyl-lower alkyl; wherein the term "heterocyclyl" is always defined as an aza-, thia-, oxa-, thiaza-, oxaza-, diaza-, triaza- or tetraza-monocycle of 3 to 8 ring members having from zero to four double bonds and optionally containing a fused benzo ring; in which radicals $X_1$ or $X_2$ respectively, the substituents optionally present are hydroxy, lower alkoxy, lower alkanoyloxy, halogen, mercapto, lower alkylthio, carboxy, lower alkoxycarbonyl, carbamoyl, N-mono- or N,N-di-lower alkylcarbamoyl, cyano, nitro, amino, lower alkylamino, di-lower-alkylamino, acylamino, diacylamino, lower alkyleneamino, phenyl or lower alkyl; where Y represents oxygen, sulfur, sulfinyl or sulfonyl; and the rings A and B are each unsubstituted or substituted by 1, 2 or 3 substituents selected from the group consisting of hydroxy, lower alkoxy, lower alkanoyloxy, lower alkylthio, amino, lower alkylamino, di-lower alkylamino, acrylamino, di-acrylamino, lower alkyl, halogen, carboxy, lower alkoxycarbonyl, carbamoyl, N-mono- or N,N-di-lower alkylcarbamoyl, cyano, nitro, sulfo, sulfamoyl, N-lower alkyl-, N,N-di-lower alkyl- or N-phenylsulfamoyl; or pharmaceutically acceptable salts of such compounds that contain a salt-forming group.

The invention relates specifically to pharmaceutical preparations containing compounds of formula I, wherein one of the radicals $X_1$ and $X_2$ is hydrogen, halogen, amino, lower-alkylamino or di-lower-alkylamino the alkyl part being optionally substituted by carboxy or lower-alkoxycarbonyl, lower alkyleneamino, aza-, oxa- or thia-lower-alkyleneamino or phenylamino, lower alkanoylamino, lower alkoxy optionally substituted by carboxy or lower alkoxycarbonyl, phenyloxy, lower alkythio optionally substituted by carboxy or lower-alkoxy carbonyl, phenylthio, phenyl-lower alkylthio or heterocyclylthio, wherein the term "heterocyclyl" is defined as an oxa-, thia- or aza-monocycle of 5 or 6 ring members having zero to three double bonds and optionally containing a fused benzo ring and optionally being substituted by formyl and/or phenyl; wherein the other of the two radicals $X_1$ and $X_2$ is formyl, imino optionally substituted by hydroxy or phenyl, carboxy, lower alkoxycarbonyl, carbamoyl, N-mono- or N,N-di-lower alkylcarbamoyl, cyano, lower alkylcarbonyl optionally substituted by halogen; or lower alkyl optionally being substituted by hydroxy; Y represents oxygen, sulfur, sulfinyl or sulfonyl but must be sulfur, sulfinyl or sulfonyl, if $X_1$ is hydrogen and $X_2$ is formyl; and the rings A and B are each unsubstituted or substituted by lower alkyl, lower alkoxy, lower alkanoyloxy, lower alkylthio, carboxy, lower alkoxycarbonyl, cyano, halogen and/or nitro; with the proviso that $X_1$ and $X_2$ cannot be together halogen and formyl; or pharmaceutically acceptable salts of such compounds that contain a salt-forming group.

The invention relates in particular to pharmaceutical preparations containing compounds of formula I, wherein one of the radicals $X_1$ and $X_2$ is hydrogen, halogen, amino, lower-alkylamino or di-lower-alkylamino the alkyl part being optionally substituted by carboxy or lower-alkoxycarbonyl, lower alkyleneamino, aza-, oxa- or thia-lower-alkyleneamino or phenylamino, lower alkoxy, lower alkylthio optionally substituted by carboxy or lower-alkoxycarbonyl, benzylthio or heterocyclylthio, wherein the term "heterocyclyl" is defined as an oxa- or thia-monocycle of 5 or 6 ring members having 1 or 2 double bonds and optionally containing a fused benzo ring and optionally being substituted by formyl and/or phenyl; wherein the other of the two radicals $X_1$ and $X_2$ is formyl; imino optionally substituted by hydroxy or phenyl, carboxy, cyano, lower alkylcarbonyl optionally substituted by halogen; or lower alkyl optionally being substituted by hydroxy; Y represents oxygen or sulfur, but must be sulfur, if $X_1$ is hydrogen and $X_2$ is formyl; and the rings A and B are each unsubstituted or substituted by lower alkyl, lower alkoxy, halogen and/or nitro; with the proviso that $X_1$ and $X_2$ cannot be altogether halogen and formyl; or pharmaceutically acceptable salts of such compounds that contain a salt-forming group.

The invention further relates to the use of the compounds of formula I for the manufacture of pharmaceutical preparations or as pharmacologically active compounds.

The invention also relates to compounds of formula I

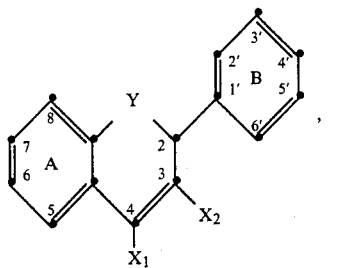

(I)

in which $X_1$ and $X_2$, independently of each other, represent hydrogen, halogen, unsubstituted or substituted amino or a quaternary ammonium salt; etherified or esterified hydroxy; free, etherified, esterified or oxidized mercapto; nitro; functionally modified formyl; free or functionally modified carboxyl; acyl; an unsubstituted or substituted hydrocarbon radical, or an unsubstituted or substituted heterocyclic radical; with the proviso that at least one of the radicals $X_1$ and $X_2$ is bonded by a carbon atom to the ring system and with the proviso that $X_1$ and $X_2$ cannot be together halogen and formyl; in which Y represents oxygen, sulfur, sulfinyl or sulfonyl, and the rings A and B are each unsubstituted or substituted; with the further provisos that Y is sulfur, sulfinyl or sulfonyl, if $X_1$ is hydrogen and $X_2$ is methyl, 2-acetoxy-2-phenylethyl, ($C_3$-$C_6$)alkyl, formyl, 2-phenylethenyl or phenyl which is optionally mono- or disubstituted by methoxy;

that Y is sulfur, sulfinyl or sulfonyl, if $X_1$ is acetyl, $X_2$ is acetoxy, A is 5,7-dimethoxy-1,2-phenylene and B is 2',3'-diacetoxyphenyl;

that Y is sulfur, sulfinyl or sulfonyl, if $X_1$ is phenyl which at least is trisubstituted, $X_2$ is acetoxy, A is 5,7-dimethoxy-1,2-phenylene and B is dimethoxyphenyl;

that Y is sulfur, sulfinyl or sulfonyl, if $X_1$ is 4-methylphenyl, $X_2$ is phenyl, A is 6-methyl-1,2-phenylene and B is phenyl;

that Y is sulfur or sulfinyl, if $X_2$ is hydrogen and $X_1$ is optionally substituted phenyl;

and salts of such compounds that contain a salt-forming group.

Preferred are compounds of formula I, in which $X_1$ and $X_2$, independently of each other, represents hydrogen, halogen, primary, secondary or tertiary amino, acylamino, di-acrylamino or a quaternary ammonium salt; unsubstituted or substituted lower-alkoxy, lower-alkenyloxy, cycloalkoxy, phenyloxy, phenyl-lower-alkoxy, heterocyclyloxy or heterocyclyl-lower alkoxy, lower-alkoxycarbonyloxy, lower alkylsulfonyloxy, phenylsulfonyloxy, formyloxy, lower-alkylcarbonyloxy or benzoyloxy; mercapto, unsubstituted or substituted lower-alkylthio, phenylthio, phenyl-lower-alkylthio, heterocyclylthio or heterocyclyl-lower alkylthio; lower-alkoxy-carbonylthio or lower-alkanoylthio; unsubstituted or substituted phenylsulfinyl, phenyl-lower-alkylsulfinyl, lower alkylsulfinyl, phenylsulfonyl, phenyl-lower-alkylsulfonyl or lower alkylsulfonyl; nitro; formyl, acetalised or semiacetalised formyl, or unsubstituted or substituted imino; free or esterified carboxyl, amidated carboxyl or cyano; unsubstituted or substituted lower alkylcarbonyl, cycloalkanoyl, benzoyl or phenyl-lower alkylcarbonyl; or a saturated or unsaturated, unsubstituted or substituted aliphatic, cycloaliphatic, cycloaliphatic-aliphatic, aromatic, aromatic-aliphatic, heterocyclic or heterocyclic-aliphatic radical; with the proviso that at least one of the radicals $X_1$ and $X_2$ is bonded by a carbon atom to the ring system and with the further proviso that $X_1$ and $X_2$ cannot be together halogen and formyl; Y represents oxygen, sulfur, sulfinyl or sulfonyl; and the rings A and B are each unsubstituted or substituted by 1, 2, 3 or 4 substituents; with the provisos that Y is sulfur, sulfinyl or sulfonyl, if $X_1$ is hydrogen and $X_2$ is formyl, lower alkyl, 2-acetoxy-2-phenylethyl, 2-phenylethenyl or phenyl which is optionally mono- or disubstituted by methoxy;

that Y is sulfur, sulfinyl or sulfonyl, if $X_2$ is acetoxy and
$X_1$ is acetyl or phenyl which at least is trisubstituted;

that X is sulfur, sulfinyl or sulfonyl, if $X_1$ is 4-methylphenyl and
$X_2$ is phenyl; and that Y is sulfur or sulfinyl, if $X_2$ is hydrogen and $X_1$ is optionally substituted phenyl;

and salts of such compounds that contain a salt-forming group.

A preferred embodiment of this invention relates to compounds of formula I, in which one of the radicals $X_1$ and $X_2$ is halogen, amino, unsubstituted or substituted lower-alkylamino, di-lower-alkylamino, cycloalkylamino, N-cycloalkyl-N-lower-alkylamino, phenylamino, N-phenyl-N-lower-alkylamino, phenyl-lower-alkylamino, N-phenyl-lower-alkyl-N-lower-alkylamino, lower alkyleneamino, aza-, oxa-, or thia-lower alkyleneamino, heterocyclylamino, heterocyclyl-lower alkylamino, lower-alkanoylamino, benzoylamino, phenyl-lower-alkylcarbonylamino or phenylhydrazino; a tri-lower-alkylammonium salt; unsubstituted or substituted lower-alkoxy, lower-alkenyloxy, phenyloxy, phenyl-lower-alkoxy, heterocyclyloxy, heterocyclyl-lower alkoxy, lower alkoxycarbonyloxy, formyloxy, ($C_2$-$C_7$)alkylcarbonyloxy or benzoyloxy; mercapto, unsubstituted or substituted alkylthio, phenylthio or phenyl-lower-alkylthio, heterocyclylthio or heterocyclyl-lower alkylthio; and wherein the other of the two radicals $X_1$ and $X_2$ represents formyl, formyl acetalised or semiacetalised by a lower alkanol, imino optionally substituted by hydroxy, lower alkoxy, lower alkyl, unsubstituted or substituted phenyl, or unsubstituted or substituted amino; carboxy, lower-alkoxycarbonyl, optionally N-lower-alkylated, N,N-di-lower-alkylated or N-phenylated carbamoyl, or cyano;

unsubstituted or substituted lower alkylcarbonyl, benzoyl or phenyl-lower-alkylcarbonyl; or an unsubstituted or substituted alkyl, alkenyl or alkynyl radical, unsubstituted or substituted cycloalkyl, cycloalkenyl, cycloalkyl-lower alkyl, cycloalkenyl-lower-alkyl, cycloalkyl-lower-alkenyl or cycloalkenyl-lower-alkenyl, or an unsubstituted or substituted phenyl or phenyl-lower-alkyl or unsubstituted or substituted heterocyclyl bonded by a carbon atom, or heterocyclyl-lower alkyl; wherein the term "heterocyclyl" is always defined as an aza-, thia-, oxa-, thiaza-, oxaza-, diaza-, triaza- or tetraza-monocycle of 3 to 8 ring members having from zero to four double bonds and optionally containing a fused benzo ring; with the proviso that $X_1$ and $X_2$ cannot be together halogen and formyl; Y represents oxygen, sulfur, sulfinyl or sulfonyl; and the rings A and B are each unsubstituted or substituted by 1, 2 or 3 substituents; and salts of such compounds that contain a salt-forming group.

Another preferred embodiment of this invention relates to compounds of formula I, in which one of the radicals $X_1$ and $X_2$ is hydrogen, and the other is formyl acetalised or semiacetalised by a lower alkanol; imino optionally substituted by hydroxy, lower alkoxy, lower alkyl, unsubstituted or substituted phenyl, or unsubstituted or substituted amino; carboxy, lower-alkoxycarbonyl, optionally N-lower-alkylated, N,N-di-lower-alkylated or N-phenylated carbamoyl, or cyano; unsubstituted or substituted lower alkylcarbonyl, benzoyl or phenyl-lower-alkylcarbonyl; or an unsubstituted or substituted alkynyl radical, unsubstituted or substituted cycloalkyl, cycloalkenyl, cycloalkyl-lower-alkyl, cycloalkenyl-lower-alkyl, cycloalkyl-lower alkenyl, cycloalkenyl-lower alkenyl, phenyl-lower-alkyl or unsubstituted or substituted heterocyclyl bonded by a carbon atom, or heterocyclyl-lower alkyl; wherein the term "heterocyclyl" is always defined as an aza-, thia-, oxa-, thiaza-, oxaza-, diaza-, triaza- or tetraza-monocycle of 3 to 8 ring members having from zero to four double bonds and optionally containing a fused benzo ring; Y represents oxygen, sulfur, sulfinyl or sulfonyl; and the rings A and B are each unsubstituted or substituted by 1, 2 or 3 substituents; and salts of such compounds that contain a salt-forming group.

Particularly preferred are those compounds of formula I, wherein one of the radicals $X_1$ and $X_2$ is halogen, amino, a tri-lower-alkylammonium salt, formyloxy, lower alkoxycarbonyloxy or mercapto; or represents optionally substituted phenylamino, phenylhydrazino, benzoylamino, phenyloxy, benzoyloxy, phenylthio, N-phenyl-N-lower-alkylamino, phenyl-lower-alkylamino, N-phenyl-lower-alkyl-N-lower-alkylamino, phenyl-lower-alkylcarbonylamino, phenyl-lower-alkoxy or phenyl-lower-alkylthio, heterocyclylamino, heterocyclyl-lower alkylamino, heterocyclyloxy, heterocyclyl-lower alkoxy, heterocyclylthio, or heterocyclyl-lower alkylthio, in which radicals $X_1$ or $X_2$ respectively, the substituents optionally present are hydroxy, lower alkoxy, lower alkanoyloxy, lower alkylthio, amino, lower alkylmino, di-lower alkylamino, acylamino, di-acylamino, lower alkyl, phenyl, halogen, formyl, carboxy, lower alkoxycarbonyl, carbamoyl, N-mono- or N,N-di-lower alkylcarbamoyl, cyano, nitro, sulfo, or sulfamoyl, N-lower-alkyl-, N,N-di-lower alkyl- or N-phenylsulfamoyl; or wherein one of the radicals $X_1$ and $X_2$ is unsubstituted or substituted lower alkylamino, di-lower alkylamino, cycloalkylamino, N-cycloalkyl-N-lower alkylamino, lower alkyleneamino, aza-, oxa- or thia-lower alkyleneamino, lower alkanoylamino, lower alkoxy, lower alkenyloxy, ($C_2$–$C_7$)-alkylcarbonyloxy or lower alkylthio, in which radicals $X_1$ or $X_2$ respectively, the substituents optionally present are hydroxy, lower alkoxy, lower alkanoyloxy, amino, lower alkylamino, di-lower alkylamino, acylamino, di-acylamino, carboxy, lower alkoxycarbonyl, carbamoyl, N-mono- or N,N-di-lower-alkylcarbamoyl, cyano or phenyl that optionally is substituted by carboxy, lower alkoxycarbonyl or cyano; and wherein the other of the two radicals $X_1$ and $X_2$ represents formyl, formyl acetalised or semiacetalised by a lower alkanol, imino optionally substituted by hydroxy, lower alkoxy, lower alkyl or amino which may be optionally substituted for its part by lower alkyl, phenyl or carbamoyl; carboxy, lower-alkoxycarbonyl, carbamoyl, N-mono- or N,N-di-lower alkylcarbamoyl or cyano; or represents an unsubstituted or substituted alkyl, alkenyl or alkynyl radical, unsubstituted or substituted cycloalkyl, cycloalkenyl, cycloalkyl-lower-alkyl, cycloalkenyl-lower-alkyl, cycloalkyl-lower-alkenyl or cycloalkenyl-lower alkenyl or an unsubstituted or substituted phenyl or phenyl-lower-alkyl radical, unsubstituted or substituted phenylimino, N-phenylated carbamoyl, lower alkylcarbonyl, benzoyl or phenyl-lower alkylcarbonyl, or unsubstituted or substituted heterocyclyl bonded by a carbon atom, or heterocyclyl-lower alkyl, in which radicals $X_1$ or $X_2$ respectively, the substituents optionally present are hydroxy, lower alkoxy, lower alkanoyloxy, halogen, mercapto, lower alkylthio, carboxy, lower alkoxycarbonyl, carbamoyl, N-mono- or N,N-di-lower alkylcarbamoyl, cyano, nitro, amino, lower alkylamino, di-lower-alkylamino, acylamino, diacylamino, lower alkyleneamino, phenyl or lower alkyl; wherein the term "heterocyclyl" is always defined as an aza-, thia-, oxa-, thiaza-, oxaza-, diaza-, triaza- or tetraza-monocycle of 3 to 8 ring members having from zero to four double bonds and optionally containing a fused benzo ring; with the proviso that $X_1$ and $X_2$ cannot be together halogen and formyl; Y represents oxygen, sulfur, sulfinyl or sulfonyl; and the rings A and B are each unsubstituted or substituted by 1, 2 or 3 substituents selected from the group consisting of hydroxy, lower alkoxy, lower alkanoyloxy, lower alkylthio, amino, lower alkylamino, di-lower alkylamino, acylamino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl, N-lower alkyl-, N,N-di-lower alkyl- or N-phenyl-sulfamoyl; and pharmaceutically acceptable salts of such compounds that contain a salt-forming group.

Also particularly preferred are those compounds of formula I, wherein one of the radicals $X_1$ and $X_2$ is hydrogen; and the other is formyl acetalised or semiacetalised by a lower alkanol, imino optionally substituted by hydroxy, lower alkoxy, lower alkyl or amino which may be optionally substituted for its part by lower alkyl, phenyl or carbamoyl; carboxy, lower-alkoxycarbonyl, carbamoyl, N-mono- or N,N-di-lower-alkylcarbamoyl or cyano; or represents an unsubstituted or substituted alkynyl radical, unsubstituted or substituted cycloalkyl, cycloalkenyl, cycloalkyl-lower-alkyl, cycloalkenyl-lower-alkyl, cycloalkyl-lower-alkenyl or cycloalkenyl-lower alkenyl, unsubstituted or substituted phenylimino, N-phenylated carbamoyl, lower alkylcarbonyl, benzoyl or phenyl-lower alkylcarbonyl, phenyl-lower alkyl or unsubstituted or substituted heterocyclyl bonded by a carbon atoms, or heterocyclyl-lower alkyl; wherein the term "heterocyclyl" is always defined as an aza-, thia-, oxa-, thiaza-, oxaza-, diaza-, triaza- or tetraza-monocycle of 3 to 8 ring members having from zero to four double bonds and optionally containing a fused benzo ring; in which radicals $X_1$ or $X_2$ respectively, the substituents optionally present are hydroxy, lower alkoxy, lower alkanoyloxy, halogen, mercapto, lower alkylthio, carboxy, lower alkoxycarbonyl, carbamoyl, N-mono- or N,N-di-lower alkylcarbamoyl, cyano, nitro, amino, lower alkylamino, di-lower-alkylamino, acylamino, diacylamino, lower alkyleneamino, phenyl or lower alkyl; wherein Y represents oxygen, sulfur, sulfinyl or sulfonyl; and the rings A and B are each unsubstituted or substituted by 1, 2 or 3 substituents selected from the group consisting of hydroxy, lower alkoxy, lower alkanoyloxy, lower alkylthio, amino, lower alkylamino, di-lower alkylamino, acylmino, di-acylamino, lower alkyl, halogen, carboxy, lower alkoxycarbonyl, carbamoyl, N-mono- or N,N-di-lower alkylcarbamoyl, cyano, nitro, sulfo, sulfamoyl, N-lower alkyl-, N,N-di-lower alkyl- or N-phenylsulfamoyl; and pharmaceutically acceptable salts of such compounds that contain a salt-forming group.

Greatly preferred are the compounds of formula I, wherein one of the radicals $X_1$ and $X_2$ is hydrogen, halogen, amino, lower-alkylamino or di-lower-alkylamino the alkyl part being optionally substituted by carboxy or lower-alkoxycarbonyl, lower alkyleneamino, aza, oxa- or thia-lower-alkyleneamino or phenylamino, lower alkanoylamino, lower alkoxy optionally substituted by carboxy or lower alkoxycarbonyl, phenyloxy, lower alkylthio optionally substituted by carboxy or lower-alkoxycarbonyl, phenylthio, phenyl-lower alkylthio or heterocyclylthio, wherein the term "heterocyclyl" is defined as an oxa-, thia- or aza-monocycle of 5 or 6 ring members having zero to three double bonds and optionally containing a fused benzo ring and optionally being substituted by formyl and/or phenyl; wherein the other of the two radicals $X_1$ and $X_2$ is formyl, imino optionally substituted by hydroxy or phenyl, carboxy, lower alkoxycarbonyl, carbamoyl, N-mono- or N,N-di-lower alkylcarbamoyl, cyano, lower alkylcarbonyl optionally substituted by halogen; or lower alkyl optionally being substituted by hydroxy; Y represents oxygen, sulfur, sulfinyl or sulfonyl but must be sulfur, sulfinyl or sulfonyl, if $X_1$ is hydrogen and $X_2$ is formyl or lower alkyl; and the rings A and B are each unsubstituted or substituted by lower alkyl, lower alkoxy, lower alkanoyloxy, lower alkylthio, carboxy, lower alkoxycarbonyl, cyano, halogen and/or nitro; with the proviso that $X_1$ and $X_2$ cannot be together halogen and formyl; or pharmaceutically acceptable salts of such compounds that contain a salt-forming group.

In general, preferred are those compounds of formula I wherein Y is oxygen or sulfur.

Also preferred are the compounds of formula I, in which $X_1$ and $X_2$, independently of each other, are hydrogen, halogen, amino, lower-alkylamino or di-lower-alkylamino the lower-alkyl part being optionally substituted by amino, lower-alkylmino, di-lower-alkylamino, free or functionally modified carboxyl; phenylamino or phenyl-lower-alkylamino the phenyl part being optionally substituted by hydroxy, lower alkoxy, lower alkyl, free or functionally modified carboxyl or halogen; N-phenyl-N-lower-alkylmino phenyl and lower-alkyl optionally being substituted as described above; lower alkyleneamino having 5 to 7 ring members; lower alkanoylamino or benzoylamino; lower alkoxy optionally substituted by functionally modified carboxyl, halogen, hydroxy, amino, lower-alkylamino, di-lower-alkylamino or epoxy; phenyloxy, phenyl-lower-alkoxy; lower alkanoyloxy, formyloxy or benzoyloxy; lower alkylthio optionally substituted by free or functionally modified carboxyl, halogen, hydroxy, amino, lower-alkylamino, di-lower-alkylamino or epoxy; phenylthio, benzylthio or a group —S—Het, wherein Het is a monocyclic or bicyclic oxa-, aza-, thia-, thiaza-, oxaza- or diaza-cyclic radical, which is saturated or unsaturated, for example of aromatic character, which contains 2–9 ring carbon atoms, and which is optionally substituted by formyl, phenyl, lower alkyl, lower alkoxy, halogen, carboxy, esterified or amidated carboxyl or cyano; formyl, imino optionally substituted by hydroxy, lower alkyl, phenyl which may be substituted for its part by lower alkyl, lower alkoxy, halogen or nitro, amino which may be substituted for its part by lower alkyl, phenyl or carbamoyl; carboxy; lower alkoxycarbonyl, or cyano; lower alkanoyl optionally substituted by halogen, benzoyl or phenyl-lower-alkanoyl optionally substituted in the benzene ring by hydroxy, halogen, lower alkyl or lower alkoxy; or a lower alkyl radical which is unsubstituted or substituted by hydroxy, oxo, amino, imino, di-lower-alkylamino, halogen, hydroxyimino, phenylimino, nitro-phenylimino, acetylimino, cyano, carboxy or lower-alkylsulfinyl; with the proviso that at least one of the radicals $X_1$ and $X_2$ is bonded by a carbon atom to the ring system and with the further proviso that $X_1$ and $X_2$ cannot be together halogen and formyl; Y is oxygen or sulfur but must be sulfur, if $X_1$ is hydrogen and $X_2$ is formyl or lower alkyl; and the rings A and B are each unsubstituted or substituted by lower alkyl, lower alkoxy, halogen or nitro; and pharmaceutically acceptable salts of such compounds that contain a salt-forming group.

Specifically preferred are the compounds of formula I, wherein one of the radicals $X_1$ and $X_2$ is hydrogen, halogen, amino, lower-alkylamino or di-lower-alkylamino the alkyl part being optionally substituted by carboxy or lower-alkoxycarbonyl, lower alkyleneamino, aza-, oxa- or thia-lower-alkyleneamino or phenylamino, lower alkoxy, lower alkylthio optionally substituted by carboxy or lower-alkoxycarbonyl, benzylthio or heterocyclylthio, wherein the term "heterocyclyl" is defined as an oxa- or thia-monocycle of 5 or 6 ring members having 1 or 2 double bonds and optionally containing a fused benzo ring and optionally being substituted by formyl and/or phenyl; wherein the other of the two radicals $X_1$ and $X_2$ is formyl, imino optionally substituted by hydroxy or phenyl, carboxy, cyano, lower alkylcarbonyl optionally substituted by halogen; or lower alkyl optionally being substituted by hydroxy; Y represents oxygen or sulfur but must be sulfur, if $X_1$ represents hydrogen and $X_2$ is formyl or lower alkyl; and the rings A and B are each unsubstituted or substituted by lower alkyl, lower alkoxy, halogen and/or nitro; with the proviso that $X_1$ and $X_2$ cannot be together halogen and formyl; and pharmaceutically acceptable salts of such compounds that contain a salt-forming group.

Of great importance are those compounds of formula I, wherein one of the radicals $X_1$ and $X_2$ is halogen, amino, lower-alkylamino or di-lower-alkylamino the alkyl part being optionally substituted by carboxy or lower-alkoxycarbonyl, lower alkyleneamino, aza-, oxa- or thia-lower-alkyleneamino or phenylamino, lower alkoxy, lower alkylthio optionally substituted by carboxy or lower-alkoxycarbonyl, benzylthio or heterocyclylthio, wherein the term "heterocyclyl" is defined as an oxa- or thia-monocycle of 5 or 6 ring members having 1 or 2 double bonds and optionally containing a fused benzo ring and optionally being substituted by formyl and/or phenyl; wherein the other of the two radicals $X_1$ and $X_2$ is formyl, imino optionally substituted by hydroxy or phenyl, carboxy, cyano, lower alkanoyl optionally substituted by halogen; or lower alkyl optionally being substituted by hydroxy; Y represents oxygen or sulfur; and the rings A and B are each unsubstituted or substituted by lower alkyl, lower alkoxy, halogen and/or nitro; with the proviso that $X_1$ and $X_2$ cannot be together halogen and formyl; and pharmaceutically acceptable salts of such compounds that contain a salt-forming group.

One preferred embodiment of the invention relates to compounds of formula I wherein the radical $X_2$ is bonded by a carbon atom to the ring system and the radical $X_1$ is not.

Another preferred embodiment of the invention relates to compounds of formula I wherein the radical $X_1$ is bonded by a carbon atom to the ring system and the radical $X_2$ is not.

The compounds most specifically preferred are: 3-formyl-4-methoxy-flav-3-ene, 4-ethoxy-3-formyl-flav-3-ene, 3-formyl-4-piperidino-flav-3-ene, 3-formyl-4-(N-morpholino)-flav-3-ene, 3-formyl-4-(N-thiomorpholino)-flav-3-ene, 4-benzylmercapto-3-formyl-flav-3-ene, 4-(2″H-3″-formyl-2″-phenyl-1″-benzopyran-4″-yl-thio)-3-formyl-flav-3-ene, 4-chloro-3-(α-hydroxyethyl)-flav-3-ene, 4-chloro-3-hydroxyiminomethyl-flav-3-ene, 4-chloro-3-cyano-flav-3-ene, 3-formyl-4-(N-methyl-N-ethoxycarbonylmethylamino)-flav-3-ene, 4-chloro-3-carboxy-flav-3-ene, 4-chloro-3-hydroxymethyl-flav-3-ene, 3-carboxy-flav-3-ene and 4-(S-carboxymethylthio)-3-formyl-flav-3-ene.

Above all are preferred the compounds of formula I described in the examples and pharmaceutically acceptable salts thereof.

The invention also relates to pharmaceutical preparations containing the novel compounds of formula I or any of the preferred embodiments thereof as described above, and also to the use thereof for the manufacture of pharmaceutical preparations or as pharmacologically active compounds.

The compounds of the present invention are obtained according to processes known per se.

Thus, the novel compounds of the formula I and salts of such compounds that have a salt-forming group, can be produced e.g. by replacing halogen and/or formyl in a compound of the formula II

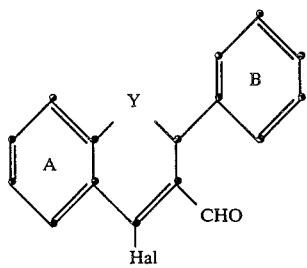

or in a compound of the formula IIa

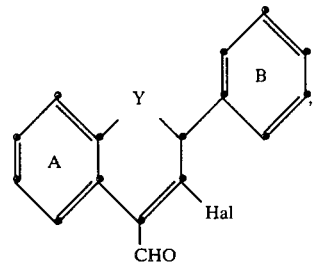

wherein Hal is halogen and A, B and Y have the meanings given under formula I, by a substituent $X_1$ and/or a substituent $X_2$, and/or, if desired, converting a resulting compound of the formula I into another compound of the formula I and/or, if desired, converting a free compound obtained into a salt, or a salt into the free compound or into another salt thereof, and, if required, resolving a mixture of isomers or racemates obtained into the single isomers or racemates, and, if required, resolving a racemate obtained into the optical antipodes.

Compounds of the formula I, wherein $X_2$ is a hydrocarbon radical, free or functionally modified carboxyl, acyl or functionally modified formyl, and $X_1$ is halogen, can be manufactured in a conventional manner, for example by replacing in 3-position of a compound of the formula II formyl by one of the above mentioned substituents $X_2$.

The replacement of formyl in 3-position of a compound of the formula II by methyl can be effected for example by a conventional reduction method, such as by a process according to Wolff-Kishner (cp. Houben-Weyl, Methoden der Org. Chemie, 4th Edition, Vol. VII/1, pp. 491–492) using e.g. hydrazine hydrate and alkali metal hydroxide, for example potassium or sodium hydroxide, in an inert high-boiling solvent, such as diethylenglycol or triethylenglycol, or e.g. by a process according to Clemmensen (cp. Houben-Weyl, 4th Edition, Vol. VII/1, p. 491) which is characterised by the action of amalgated zinc and concentrated hydrohalic acid, preferably hydrochloric acid, on the formyl compound (cp. Houben-Weyl, Methoden der Org. Chemie, 4th Edition, Vol. VII/1, pp. 491–494).

Compounds of the formula I in which $X_2$ is hydroxymethyl can also be obtained e.g. by reducing the formyl group within a compound of formula II. The reduction can be effected in a manner known per se, for example by catalytically activated or nascent hydrogen. The reduction can also be performed e.g. with the aid of metal hydrides, for example aluminium hydride or boron hydride and diborane, especially however with complex metal hydrides, such as lithium aluminium hyride, sodium borohydride or lithium tritert-butoxyaluminium hydride. Reduction of the compounds of the formula I can also be performed e.g. according to Meerwein-Ponndorf-Verley with use of a secondary alcohol, for example isopropanol, in the presence of e.g. aluminium triisopropylate. As solvents can be used e.g. aromatic hydrocarbons, such as benzene or toluene [cp. Houben-Weyl, Methoden der Org. Chemie, 4th Edition, Vol. 7/1, 1086 (1954), C. H. Synder, M. Micklus, J. Org. Chem., 35, 264 (1970)].

Compounds of the formula II can be converted into compounds of the formula I, wherein $X_2$ is unsubstituted oxiranyl, acetyl or formylmethyl and $X_1$ is halogen, e.g. by reacting a corresponding starting material of the formula II with diazomethane, and converting the resulting diazonium-betain compound, in a manner known per se, into compounds of the formula I, wherein $X_2$ has the above given meanings [cp. B. Eistert, Ang. Chem. 54, 99, 124 (1941); Ang. Chem. 55, 118 (1942)].

Compounds of the formula II can be converted into compounds of the formula I, in which $X_2$ is a [2,2-di-(lower-alkoxycarbonyl)-vinyl]group, where a lower-alkoxycarbonyl group in the substituent can be in each case also replaced by cyano, carboxy or amido, and $X_1$ is halogen, e.g. by reacting a compound of the formula II with a malonic acid derivative, for example malonic acid diethyl ester, cyanoacetic acid and esters and amides thereof, malonic acid, malonnitrile, malonamide or malonmonoamide ester, e.g. in the presence of a slightly basic catalyst, such as ammonia, secondary and tertiary amines, for example di- or triethylamine, piperidine and pyridine [cp. G. Jones, Org. Reactions 15, 204 (1967); E. Knoevenagel, Ber. dtsch. chem. Ges. 29 (1896) 121; 31 (1898) 2598; 37 (1904) 4461; Doebner, Ber. dtsch. chem. Ges. 33 (1900) 2140; 35 (1902) 1137].

It is possible to use as starting materials for the reaction, in place of the malonic acid derivatives listed above, also other compounds having an activated methylene group, for example acetoacetic acid esters and β-diketones, and also analogs in which one or both carbonyls are replaced by sulfo groups, as well as nitroalkanes.

Compounds of the formula II can also be converted into compounds of the formula I, wherein $X_2$ is an unsubstituted or substituted carboxyethenyl group and $X_1$ is halogen, e.g. by reacting a compound of the formula II with e.g. acetic anhydride or with the anhydride of a substituted acetic acid preferably in the presence of a basic condensing agent, especially sodium acetate [cp. J. R. Johnson, Organic Reactions 1, 210 (1942); H. O. House, Modern Synthetic Reactions, 2nd Ed., (W. A. Benjamin, California, 1972), pp. 660-663; P. H. Leake, Chem. Reviews 56 (1956) 27].

Compounds of the formula II can be converted into compounds of the formula I, wherein $X_2$ is a 1-hydroxy-1-cyanomethyl radical or an unsubstituted or substituted 1-amino-1-cyanomethyl radical and $X_1$ is halogen, e.g. by reacting a compound of the formula II with a reagent releasing hydrogen cyanide, for example with an alkali cyanide, especially potassium cyanide, e.g. in the presence of acetic acid, or e.g. with anhydrous hydrogen cyanide preferably in the presence of an alkaline catalyst, for example a potassium hydroxide solution [cp. H. H. Hustedt and E. Pfeil, Liebigs Ann. Chem. 640 (1961) 15; A. J. Ulte, Receuil Trav. chim. Pays-Bas, 28 (1909) 1, 248, 257; Ber. dtsch. chem. Ges. 39 (1906) 1856], or e.g. with hydrogen cyanide, or with a reagent releasing this, in the presence of e.g. ammonia or a primary or secondary amine [cp. A. Strecker, Liebigs Ann. Chem. 75 (1980) 27; 91 (1854) 349; or Migrdichian, The Chemistry of Organic Cyanogen Compounds (New York 1947) p. 198], or e.g. with trimethylsilyl cyanide followed by acidic hydrolysis.

Furthermore, compounds of the formula II can be converted into compounds of the formula I, wherein $X_2$ is 1-hydroxyethyl or ethenyl, which both are substituted in 2-position by an acyl radical defined as above under the formula I, and $X_1$ is halogen, e.g. by reacting a compound of formula II in an aldol-type addition or condensation reaction with a ketone or an aldehyde having at least one hydrogen at the α-carbon atom, preferably in the presence of a base or an acid, according to Houben-Weyl, Methoden der Org. Chemie, 4th Edition, Vol. VII/2b, pp. 1449-1529 (1976).

According to a further process variant, compounds of the formula II can be converted into compounds of the formula I having 1-hydroxy-2-methylsulfinyl-ethyl and/or 2-methylsulfinyl-ethenyl as $X_2$ and halogen as $X_1$ e.g. by reacting a compound of formula II with dimethyl sulfoxide preferably in the presence of a strong base, for example an alkali hydroxide, such as sodium hydroxide, or e.g. with the reaction product of dimethyl sulfoxide and the strong base [cp. dimethyl sulfoxide, Dieter Martin et al., Akademie Verlag (1971) pp. 344-366].

Compounds of the formula II can be converted into compounds of the formula I, wherein $X_2$ is an unsubstituted or substituted 2-lower-alkoxycarbonylethenyl and $X_1$ is halogen, e.g. by reacting a compound of formula II with an unsubstituted or substituted acetic acid lower alkyl ester advantageously in the presence of an alkaline condensing agent, for example metallic sodium or sodium hydroxide [cp. Houben-Weyl-Müller 8, (1952) 514, 4 II (1955) 25; Org. Reactions, Vol. 16, 1; H. O. House, Modern Synthetic Reactions, 2nd Edition (W. A. Benjamin, California, 1972), pp. 632-639; and J. A. Fine, Ph. Pulaski, J. Org. Chem. 38, 1747 (1973)].

Furthermore, compounds of the formula II can be converted into compounds of the formula I, wherein $X_2$ is an unsubstituted or substituted α-hydroxy hydrocarbon radical and $X_1$ is halogen, e.g. by reacting a compound of formula II with an organometal compound, particularly an organo-magnesium, organo-cadmium, organo-zinc or organo-lithium compound obtained for example from a corresponding halogenated hydrocarbon radical, and decomposing the intermediate product obtained to the corresponding compound of the formula I, in which $X_2$ is an unsubstituted or substituted α-hydroxy hydrocarbon radical and $X_1$ is halogen (cp. Houben Weyl, 4th Edition, Vol. VI/1a/2, pp. 929-1021).

Compounds of the formula II can also be converted into compounds of the formula I, wherein $X_2$ is an unsaturated radical at the linkage point, for example an unsubstituted or substituted ethenyl compound, and $X_1$ is halogen, e.g. by reacting a corresponding compound of formula II with e.g. a triphenylphosphinemethylene compound, which is unsubstituted or substituted in the methylene part, or with a reagent releasing this triphenylphosphinemethylene, for example triphenylphosphinemethyl bromide, in the presence of e.g. phenyl lithium (cp. G. Wittig and U. Schöllkopf, Ber. 87, 1318 (1954); G. Wittig and W. Haag, ibid. 88, 1654 (1955).

Compounds of the formula II can be converted into compounds of the formula I, wherein $X_2$ is an unsubstituted or substituted 2-lower-alkoxycarbonyl-1-hydroxyethyl group or 2-lower-alkoxycarbonylvinyl and $X_1$ is halogen e.g. by reacting a compound of formula II with an unsubstituted or substituted haloacetic acid ester, particularly bromoacetic acid-lower-alkyl ester, e.g. in the presence of metallic zinc in an inert solvent, for example ether, benzene, toluene or tetrahydrofuran, and hydrolysing the organic zinc compound obtained to give a β-hydroxycarboxylic acid ester, and then optionally dehydrating this to the unsaturated compound, in which $X_2$ is an unsubstituted or substituted 2-lower-alkoxycarbonylvinyl radical and $X_1$ is halogen. The reaction can be catalysed e.g. by small additions of elementary iodine. E.g. metallic lithium can also be used, in place of metallic zinc, for producing an organolithium compound [cp. R. L. Shriner, Organic Reactions 1, 1 (1942); D. G. M. Diaper, A. Kuksis, Chem. Rev. 59, 89 (1959); H. O. House, Modern Synthetic Reactions, 2nd Ed. (W. A. Benjamin, California, 1972), pp. 671–682; M. Gaudemar, Organometal. Chem. Rev. Sect. A 8, 183 (1972); M. W. Rathke, Organic Reactions 22, 423 (1975); A. Balsamo et al., Tetrahedron Letters 1974, 1005; J. F. Ruppert, J. D. White, J. Org. Chem. 39, 269 (1974); J. E. Baldwin, J. A. Walker, Chem. Commun. 1973, 117; A. P. Krapcho et al., J. Org. Chem. 39, 1322, 1650 (1974); Tetrahedron Letters 1974, 2721].

Compounds of the formula II can be converted into compounds of the formula I, wherein $X_2$ is a 1-hydroxy-2-nitro-lower-alkyl radical or a 2-nitro-1-lower-alkenyl radical and $X_1$ is halogen, e.g. by reacting a corresponding compound of formula II with a nitro-lower-alkane in the presence of an organic or inorganic base, for example pyridine or piperidine, a basic ion-exchanger resin, such as Amberlite ® IRA 400, or sodium hydroxide, and optionally hydrogenating the compound of the formula I obtained, by which means there are obtained compounds of the formula I, in which $X_2$ is a 2-nitro-lower-alkyl group or, on continuation of hydrogenation, a 2-amino-lower-alkyl group and $X_1$ is halogen [cp. C. J. Schmidle, R. C. Mansfield, Ind. Engng. Chem. 44, 1388 (1952); C. A. Sprang, E. F. Degering, J. Amer. Chem. Soc. 64, 1063 (1942); H. B. Hass, F. Riley, The Nitroparaffins, Chem. Reviews 32, 373–420 (1943)].

Compounds of the formula II can be converted into compounds of the formula I, in which $X_2$ is unsubstituted or mono- or disubstituted carbamoyl or lower alkoxycarbonyl and $X_1$ is halogen, e.g. by reacting a compound of formula II, e.g. in the presence of an alkali metal cyanide and a selective oxidising agent, particularly manganese dioxide, with ammonia or with a primary or secondary amine or a lower alkanol (cp. U.S. Pat. No. 3,948,931).

Compounds of the formula II can be converted into compounds of the formula I, wherein $X_2$ is cyano and $X_1$ is halogen, e.g. by reacting corresponding compounds of the formula II with hydrazoic acid in the presence or absence of additional inorganic acids, for example mineral acids, such as hydrochloric acid or, in particular, sulfuric acid [H. Wolff, Organic Reactions 3, 307 (1946)].

Compounds of the formula II can be oxidised to compounds of the formula I, wherein $X_2$ is carboxy and $X_1$ is halogen by methods known per se, for example with selenium dioxide and hydrogen peroxide (90% solution in water), e.g. in the presence of tert-butanol according to Chem. Communications 1969, pp. 345–346, or e.g. with sodium chlorite and sodium dihydrogenophosphate in a mixture of e.g. tert-butanol and 2-methylbut-2-ene, or e.g. with silver nitrate in e.g. a mixture of water and a lower alkanol preferably in the presence of an alkalimetall hydroxide, such as sodium hydroxide.

Compounds of the formula II can be further oxidised to compounds of the formula I, wherein $X_2$ is methoxycarbonyl and $X_1$ is halogen, e.g. by reaction with sodium cyanide, manganese dioxide and methanol in acetic acid according to J. Amer. Chem. Soc. 102, 6519 (1980).

Compounds of the formula I, wherein $X_2$ is cyano and $X_1$ is halogen, can be obtained from compounds of the formula II, for example by treatment with O,N-bis-(trifluoroacetyl)-hydroxylamine and pyridine in the presence of a solvent, for example benzene, according to J. Amer. Chem. Soc., 81, pp. 6340–6341 (1959).

Compounds of the formula II can be converted, in a manner known per se, into compounds of the formula I, in which $X_1$ is halogen and $X_2$ is a free or functionally modified formyl group, for example acetal, oxime, semicarbazone, thiosemicarbazone, hydrazone, oxime ether or unsubstituted or substituted imine, for example the radical of a Schiff base [cp. Chemiker Zeitung "Addition an die Carbonylgruppe" 80, 379 (1956); Weygand, Hilgetag, Org. Chem. Experimentierkunst, Leipzig 1970, 4th Ed., 391–396 and 517–528]. Treatment of a compound of the formula II with a carbonic acid derivative that contains at least one unsubstituted amido group leads to compounds of the formula I, wherein $X_2$ is imino substituted by free or functionally modified carboxyl, for example ethoxycarbonylimino or N,N-dialkyl-substituted carbamoylimino, and $X_1$ is halogen.

Compounds of the formula II can be converted into compounds of the forula I, wherein $X_2$ is acyl and $X_1$ is halogen, e.g. by first treating them with trimethylsilyl cyanide, reacting the resulting 1-trimethylsilyloxy-1-cyanomethyl compound first with a strong base, e.g. lithium diisopropylamide, then with an alkyl or aryl halide, and finally hydrolysing with an acid, e.g. hydrochloric acid to the desired acyl compound of the formula I according to Chem. Ber. 112, 2045 (1979). Instead of the 1-trimethylsilyloxy-1-cyanomethyl intermediate, it is also possible to use a corresponding dithioketal, which can be obtained e.g. by reaction of a compound of formula II with e.g. 1,2-dimercaptoethane, in the reactions described according to J. Org. Chem. 40, 231 (1975).

Compounds of the formula I, wherein $X_1$ is hydrogen, unsubstituted or substituted amino, a quaternary ammonium salt, free or etherified hydroxy, free or etherified mercapto, thiocyanato, acyl, free or functionally modified carboxyl, or an unsubstituted or substituted hydrocarbon radical, and $X_2$ is formyl, can be manufactured in a conventional manner, for example by replacing in 4-position of a compound of the formula II halogen by one of the above mentioned substituents $X_1$.

The replacement of halogen in 4-position of a compound of the formula II by hydrogen can be effected for example by the reduction of a compound of the formula II with the system sodium-tert-butanol-tetrahydrofurane according to J. Amer. Chem. Soc. 90, p. 3594 (1968) or e.g. with sodium in liquid ammonia in a Birch-type reduction [cp. Houben-Weyl, Methoden der Org. Chemie, Vol. V/1b, 4th Edition, pp. 621–625].

Compounds of the formula II can be converted into compounds of the formula I, wherein $X_1$ is unsubstituted or substituted amino, a quaternary ammonium salt, free or etherified hydroxy, free or etherified mercapto, thiocyanato or cyano and $X_2$ is formyl, in a manner known per se, for example by reaction with the corresponding nucleophiles as there are ammonia, primary or secondary amine, tertiary amine, an alkaline hydroxide, such as potassium hydroxide; a hydrocarbon or heterocyclic compound having a metallised hydroxy or mercapto group, such as sodium ethoxide or phenoxide, sodium methylmercaptide; an alkali metal thiocyanate, for example sodium thiocyanate; or a cyanide, preferably an alkali metal cyanide, such as sodium cyanide, according to Chem. Rev. 66, pp. 182–183, 186 (1966).

Furthermore, compounds of the formula II can be converted into compounds of the formula I, wherein $X_1$ is an acyl radical and $X_2$ is formyl, e.g. by converting the halogen radical in 4-position of a compound of the formula I into an organometal radical, particularly into an organomagnesium, organocadmium, organozinc or organolithium radical, and reacting this compound with a reactive functional derivative, especially with a halide, anhydride, ester or nitrile, of an aliphatic, cycloaliphatic, cycloaliphatic-aliphatic, aromatic or aromatic-aliphatic carboxylic acid, and decomposing the intermediate product obtained to the corresponding compound of the formula I, in which $X_1$ is an acyl group and $X_2$ is formyl (cp. Houben-Weyl, 4th Edition, Vol. 7/2a, pp. 558–597; and Org. React. 8, 28).

Compounds of the formula II can be converted into compounds of the formula I, wherein $X_1$ is free or functionally modified carboxyl, especially into an ester or a monosubstituted amide, and $X_2$ is formyl, e.g. by converting the halogen radical of formula I into an organometal radical, particularly into an organomagnesium, organocadmium, organozinc or organolithium radical, and reacting this e.g. with a reactive derivative of carbonic acid, especially carbon dioxide, a carbonic ester halide or an isocyanate, or with carbon monoxide [cp. J. Org. Chem. 24, 504 (1959); J. Am. Chem. Soc. 61, 1371 (1939); and Bull. Chem. Soc. Jap. 40, 2203 (1967)].

Compounds of the formula II can be converted into compounds of the formula I, wherein $X_1$ is an unsubstituted or substituted hydrocarbon radical, particularly an unsubstituted alkyl, aryl-lower-alkyl or aryl radical, and $X_2$ is formyl, e.g. by reacting a compound of formula II with an organometallic compound of the hydrocarbon radical to be introduced. For example, organoalkali metal or organoalkaline-earthmetal compounds, for example organolithium and organosodium compounds or organomagnesium compounds, can be reacted by the processes described in Houben-Weyl (4th Edition), Vol. 7/2a, pp. 486–502 [cp. J. Am. Chem. Soc. 90, 2423 (1968); Tetrahedron Letters 26, 4041 (1970); J. Am. Chem. Soc., 51, 1483 (1929): J. Am. Chem. Soc. 60, 2598 (1938)]. According to the stated references, it is also possible in each case for two halogen compounds, corresponding to the radicals to be reacted, to be reacted e.g. in the presence of an alkali metal or alkaline-earth metal, or in the presence of compound releasing one of these, for example butyl lithium, where the reaction proceeds by way of an organometallic compound as intermediate step. The organometallic compounds used can, however, also be for example organoaluminium, organocopper-lithium or organomanganese-lithium compounds [cp. J. Org. Chem. 35, 532 (1970); J. Am. Chem. Soc., 90, 5615 (1968); and Tetrahedron Letters (1970), 315].

The starting materials of the formula II can be prepared in a manner known per se.

Thus, compounds of formula II can be obtained e.g. by reaction of a compound of the formula III

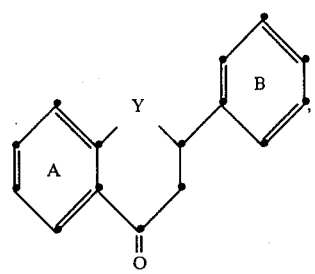

in which A, B and Y have meanings as given under formula I, with e.g. phosphorous oxyhalide, $PO(Hal)_3$, for example phosphorus oxychloride, and a formamide of the general formula IV

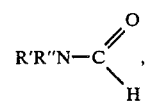

in which R' and R" is hydrogen, lower alkyl or phenyl, or in which R' and R" are together lower alkylene (Arnold-Vilsmeier-reaction) according to Böhme and Viehe, Adv. in Org. Chem. Vol. 9, I, pp. 274–298.

In a compound of the formula IV lower alkyl is for example methyl, and lower alkylene as R' and R" taken together for example pentylene. The Vilsmeier-reaction can be performed for example according to Houben-Weyl, 4th Edition, Vol. 7/1, pp. 29–36, and Chem. Ber.60, 121 (1927). Most suitable as formylating agent is dimethylformamide. As further modifications, suitable formylating agents are e.g. formamide, formylpiperidine and formyl-monomethylaniline. The phosphorous oxychloride used here can be successfully replaced in some cases by e.g. phosgene or thionylchloride according to Böhme and Viehe, Adv. in Org. Chem., Vol. 9, I, pp. 229–232.

Starting materials of the formula III are known or, if novel, can be prepared analogous to known compounds.

Compounds of the formula I obtained can be converted into other compounds of the formula I in a manner known per se.

Compounds of the formula I, wherein $X_2$ is a hydrocarbon radical, free or functionally modified carboxyl, acyl or functionally modified formyl, and $X_1$ is hydrogen, unsubstituted or substituted amino, a quaternary ammonium salt, free or etherified hydroxy, free or etherified mercapto, thiocyanato, acyl, free or functionally modified carboxyl, or an unsubstituted or substituted hydrocarbon radical, and A, B and Y have the meanings given under formula I, can be obtained from other compounds of the formula I, wherein $X_2$ is formyl, $X_1$ has all the meanings given above for $X_1$, and A, B and Y have meaning as given under formula I, e.g. by applying the same methods described above for the replacement of formyl in 3-position of a compound of the formula II yielding compounds of the formula I, wherein $X_2$ is a hydrocarbon radical, free or functionally modified carboxyl, acyl or functionally modified formyl, $X_1$ is halogen, and A, B and Y have the meanings given under formula I.

Likewise, compounds of the formula I, wherein $X_1$ is hydrogen, unsubstituted or substituted amino, a quaternary ammonium salt, free or etherified hydroxy, free or etherified mercapto, thiocyanato, acyl, free or functionally modified carboxyl, or an unsubstituted or substituted hydrocarbon radical, $X_2$ is free or functionally modified carboxyl, acyl or functionally modified formyl, and A, B and Y have the meanings given under formula I, can be obtained from other compounds of the formula I, wherein $X_1$ is halogen, $X_2$ has all the meanings given above for $X_2$, and A, B and Y have meaning as given under formula I, e.g., by applying the same methods described above for the replacement of halogen in 4-position of a compound of the formula II yielding compounds of the formula I, wherein $X_1$ is hydrogen, unsubstituted or substituted amino, a quaternary ammonium salt, free or etherified hydroxy, free or etherified mercapto, thiocyanato, acyl, free or functionally modified carboxyl, or an unsubstituted or substituted hydrocarbon radical, $X_2$ is formyl, and A, B and Y have the meanings given under formula I.

Compounds of the formula I, wherein $X_1$ is a hydrocarbon radical, free or functionally modified carboxyl, acyl, or functionally modified formyl, and $X_2$ is halogen, can be manufactured in a conventional manner, for example by replacing in 4-position of a compound of the formula IIa formyl by one of the above mentioned substituents $X_1$ in essentially the same manner as described above for the conversions of compounds of the formula II to compounds of the formula I, wherein $X_2$ has all the meanings given above for $X_1$, and $X_1$ is halogen.

Likewise, compounds of the formula I, wherein $X_2$ is hydrogen, unsubstituted or substituted amino, quaternary ammonium salt, free or etherified hydroxy, free or etherified mercapto, thiocyanato, acyl, free or functionally modified carboxyl, or an unsubstituted or substituted hydrocarbon radical, and $X_1$ is formyl, can be manufactured in a conventional manner, for example by replacing in 3-position of a compound of the formula IIa halogen by one of the above mentioned substituents $X_2$ in essentially the same manner as described above for the convertions of compounds of the formula II to compounds of the formula I, wherein $X_1$ has all the meanings given above for $X_2$, and $X_2$ is formyl.

The starting materials of the formula IIa can be prepared in a manner known per se.

Thus, compounds of formula IIa can be obtained e.g. by reaction of a compound of the formula IIIa

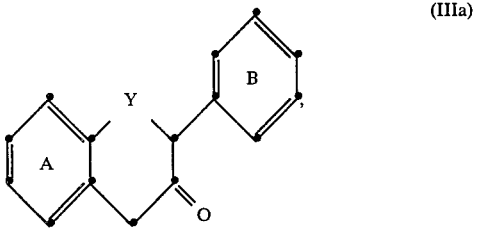

(IIIa)

wherein A, B and Y have meaning as given under formula I, with e.g. a phosphorus oxyhalide PO(Hal)$_3$ and a formamide of the formula IV in essentially the same manner as described above in detail for the production of compounds of the formula II starting from compounds of the formula III.

The starting materials of the formula IIIa are known or, if novel, can be prepared by methods known per se, for example according to Can. J. Chem. 60, 243 (1982), Austr. J. Chem. 29, 2485 (1976) or ibid. 26, 2675 (1973). One possibility of preparing compounds of formula IIIa is the oxidation of corresponding 3-hydroxy-(thio)flavanes, e.g. in a Pfitzner-Moffat type oxidation using e.g. dimethyl sulfoxide, dicyclohexylcarbodiimide and a proton source, e.g. pyridinium trifluoroacetate.

Compounds of the formulae III and IIIa, wherein Y is sulfinyl, and A and B have the meanings defined under formula I, can be produced e.g. by oxidation of corresponding compounds of the formulae III and IIIa, wherein Y is sulfur, and A and B have the meanings defined under the formula I, in the usual manner. The oxidation to sulfinyl can be effected for example by inorganic peracids, such as peracids or mineral acids, for example periodic acid or persulfuric acid; organic peracids, such as percarboxylic acid or persulfonic acids, for example performic, peracetic or trifluoroperacetic acid, m-chloroperbenzoic acid or p-toluenepersulfonic acid; by mixtures consisting of hydrogen peroxide and acids, for example mixtures of hydrogen peroxide and acetic acid.

The oxidation is often carried out in the presence of suitable catalysts, for example acids, which are suitable as catalysts, such as optionally substituted carboxylic acids, for example acetic or trifluoroacetic acid, or oxides of transition metals, such as the oxides of the elements of the auxiliary group VII, for example vanadium, molybdenum or tungsten oxide.

Compounds of the formulae III and IIIa, wherein Y is sulfonyl, and A and B have the meanings defined under formula I, can be obtained e.g. by oxidation of corresponding compounds of the formulae III and IIIa, wherein Y is sulfur or sulfinyl, and A and B have the meanings defined under the formula I, for example with dinitrogentetroxide as a catalyst, in the presence of oxygen, preferably at low temperature, using the same oxidation means as just described above for the oxidation to sulfinyl, but usually taking an excess of them.

On the contrary, compounds of the formulae III and IIIa, wherein Y is sulfinyl or sulfonyl, can be reduced to corresponding compounds of the formulae III and IIIa, wherein Y is sulfur. A suitable reduction means is for example catalytically activated hydrogen using nobel metals or their oxides as catalysts, such as palladium, platinum or rhodium or their oxides, respectively, which are optionally distributed on a suitable carrier, such as charcoal or barium sulfate.

Furthermore, reducing metal cations, such as tin(II), lead(II), copper(I), manganese(II), titanium(II), vanadium(II), molybdenum(III) or tungsten(III) compounds; hydrogen halide, such as hydrogen chloride, bromide or iodide; hydrides, such as complex metal hydrides, for example lithiumaluminium, sodiumboron or tributyltin hydride; phosphorous compounds, such as phosphorous halides, for example phosphorous trichloride or -tribromide, phosphorous pentachloride or -oxychloride; phosphines, such as triphenylphosphine, or phosphorous pentasulfide-pyridine; or sulfur compounds, such as mercaptanes, thioacids, thiophosphorous acids or dithiocarboxylic acids, dithionite or sulfur complexes, such as the iodine-pyridine-sulfurdioxide complex, can be used as reducing agents.

It is also possible in essentially the same manner as described above for compounds of the formulae III and IIIa to convert compounds of the formulae I, II, and IIa, wherein Y is sulfur, sulfinyl or sulfonyl, and A, B, Hal, $X_1$ and $X_2$ have the meanings given under the formulae I, II and IIa, into other compounds of the formulae I, II and IIa, wherein Y is sulfinyl, sulfonyl or sulfur, provided that functional groups present which are sensitive to the above-described oxidation and reduction methods are protected by conventional protecting groups described below.

Generally, in starting materials of the formulae II, IIa, III, IIIa, V, Va, VI, VIa, as well as in compounds of the formula I to be converted into another compound of the formula I, functional groups present, especially formyl, carboxy, amino, hydroxy and mercapto groups, and also sulfo groups, are optionally protected by conventional protecting groups that are customary in preparative organic chemistry. Protected formyl, carboxy, amino, hydroxy, mercapto and sulfo groups are those that can be converted under mild conditions into free formyl, carboxy, amino, hydroxy, mercapto and sulfo groups without the molecular framework being destroyed or other undesired side reactions taking place.

The purpose of introducing protecting groups is to protect the functional groups from undesired reactions with reaction components and thus prevent them of being removed or converted into a derivative.

On the other hand, reaction components can be consumed or bonded in an undesired manner by reaction with an unprotected functional group and are then no longer available for the actual reaction. The choice of protecting groups for a particular reaction depends on the nature of the functional group to be protected (carboxy group, amino group etc.), the structure and stability of the molecule of which the substituents is the functional group, and the reaction conditions.

Protecting groups that meet these conditions and their introduction and removal are known and are described, for example, in J. F. W. McOmie, "Protective Groups in Organic Chemistry", Plenum Press, London, New York 1973, T. W. Greene, "Protective Groups in Organic Synthesis", Wiley, New York 1981, and also in "The Peptides", Vol. I, Schroeder and Luebke, Academic Press, London, New York 1965, as well as in Houben-Weyl, "Methoden der Organischen Chemie", Vol. 15/1, Georg Thieme Verlag, Stuttgart, 1974.

Compounds of the formula I, wherein $X_1$ is a hydrocarbon radical, free or functionally modified carboxyl, acyl or functionally modified formyl, and $X_2$ is hydrogen, unsubstituted or substituted amino, a quaternary ammonium salt, free or etherified hydroxy, free or etherified mercapto, thiocyanato, acyl, free or functionally modified carboxyl, or an unsubstituted or substituted hydrocarbon radical, and A, B and Y have the meanings given under formula I, can be obtained e.g. from other compounds of the formula I, wherein $X_1$ is formyl, $X_2$ has all the meanings given above for $X_2$, and A, B and Y have meanings as given under formula I, e.g. by applying the same methods described above for the replacement of formyl in 4-position of a compound of the formula IIa, yielding compounds of the formula I, wherein $X_1$ is a hydrocarbon radical, free or functionally modified carboxyl, acyl or functionally modified formyl, $X_2$ is halogen, and A, B and Y have the meanings given under formula I.

Likewise, compounds of the formula I, wherein $X_2$ is hydrogen, unsubstituted or substituted amino, a quaternary ammonium salt, free or etherified hydroxy, free or etherified mercapto, thiocyanato, acyl, free or functionally modified carboxyl, or an unsubstituted or substituted hydrocarbon radical, $X_1$ is free or functionally modified carboxyl, acyl or functionally modified formyl, and A, B and Y have the meanings given under formula I, can be obtained from other compounds of the formula I, wherein $X_2$ is halogen, $X_1$ has all the meanings given above for $X_1$, and A, B and Y have meaning as given under formula I, e.g. by applying the same methods described above for the replacement of halogen in 3-position of a compound of the formula IIa yielding compounds of the formula I, wherein $X_2$ is hydrogen, unsubstituted or substituted amino, a quaternary ammonium salt, free or etherified hydroxy, free or etherified mercapto, thiocyanato, acyl, free or functionally modified carboxyl, or an unsubstituted or substituted hydrocarbon radical, $X_1$ is formyl, and A, B and Y have the meanings given under formula I.

Compounds of the formula I, wherein one of the symbols $X_1$ and $X_2$ is chlorine and the other is substituted carbamoyl, can be obtained e.g. from a compound of the formula III or the formula IIIa, respectively, by reaction with e.g. a dihalomethylene-di-lower-alkylammonium halide, such as dichloromethylene-dimethylammonium chloride, $Cl_2C=N^{\oplus}(CH_3)_2Cl^{\ominus}$, according to Angew. Chemie Int. Ed. Engl. 1971, pp. 575–576.

Compounds of the formula I, wherein one of the symbols $X_1$ and $X_2$ is di-loweralkylamino or lower alkoxy and the other is formyl, can be produced e.g. by reacting a compound of the formula V or Va, respectively,

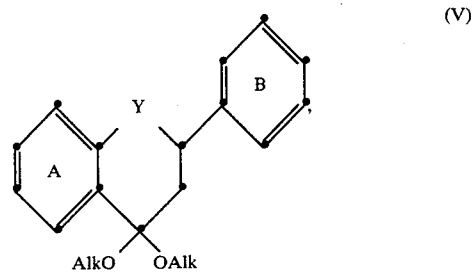

(V)

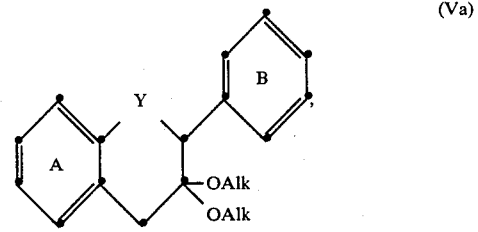

(Va)

wherein Alk is lower alkyl, for example methyl or ethyl, A, B and Y have the meanings given under formula I, with a halomethylenedilower-alkyl-iminium halide, for example chloromethylenedilower-alkyliminium chloride, $ClCH=N^{\oplus}(CH_3)_2Cl^{\ominus}$, according to Adv. in Org. Chem. (edited by E. G. Taylor), Vol. 9, Part 1, pp. 266–271 (1976).

The starting materials of the formula V and Va can be prepared by methods known per se, for example by treating compounds of the formulae III or IIIa, respectively, with lower alkanols, preferably in the presence of an acid, for example phosphoric acid, according to conventional methods of ketal formation.

Compounds of the formula I, wherein one of the symbols $X_1$ and $X_2$ is lower alkoxy, di-lower-alkylamino or N-lower-alkyl-N-phenylamino, and the other is formyl, can be obtained e.g. from a compound of formula VI or the formula VIa, respectively

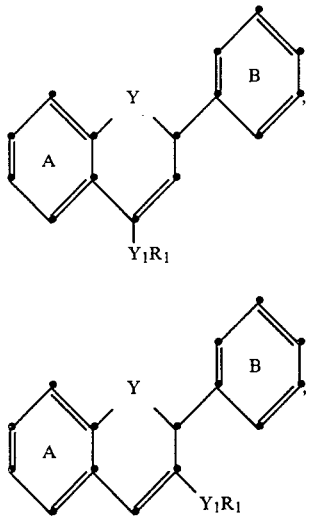

(VI)

(VIa)

wherein $R_1$ is lower alkyl, $Y_1$ is oxygen and A, B and Y have the meanings given under formula I, by reaction e.g. with halomethylene-di-lower-alkyliminium halide or halomethylene-N-lower-alkyl-N-phenyliminium halide, such as chloromethylenedimethyliminium chloride or chloro-N-methyl-N-phenyliminium chloride according to Adv. in Org. Chem. (edited by E. C. Taylor), Vol. 9, Part 1, pp. 269–271 (1976).

Compounds of formula I, wherein one of the symbols $X_1$ and $X_2$ is trihaloacetyl and the other is e.g. lower alkoxy, lower alkylthio, aryloxy or arylthio, can be obtained e.g. from a compound of formula VI or VIa, respectively, wherein $R_1$ is lower alkyl or aryl, $Y_1$ is oxygen or sulfur, and A, B and Y have meaning as given under formula I, by reaction with e.g. a trihaloacetyl halide or trihaloacetic anhydride, such as trifluoro- or trichloroacetyl chloride or trifluoro- or trichloroacetic anhydride, according to M. Hojo et al., Chemistry Letters 1976, pp. 499–502.

The starting materials of the formula VI and VIa can be obtained for example by azeotropic distillation in the presence of an acid, e.g. p-toluenesulfonic acid, of compounds of the formulae V or Va, respectively, or their thio analogs, which lose one molecule of lower alkanol or lower alkanthiol respectively, under these conditions.

Compounds of the formula I obtained can be converted into other compounds of the formula I in a manner known per se.

Compounds of the formula I, in which one of the symbols $X_1$ and $X_2$ is mono- or disubstituted amino and the other is free or functionally modified formyl, free or functionally modified carboxyl or acyl can be obtained e.g. from corresponding compounds of formula I, in which one of the symbols $X_1$ and $X_2$ is unsubstituted or substituted amino and the other is free or functionally modified formyl, free or functionally modified carboxyl or acyl by reaction e.g. with primary and secondary amines e.g. in benzene according to Bull. Chem. Soc. Jap. 52, 1735 (1979), preferably in a sealed tube.

A further process variant for the manufacture of compounds of the formula In in which one of the symbols $X_1$ and $X_2$ is mono- or disubstituted amino consists of the alkylation of corresponding compounds of the formula I, in which one of the symbols $X_1$ and $X_2$ is unsubstituted or monosubstituted amiono, by alkylation means, for example alkyltosylates, such as methyltosylate, advantageously in the presence of a base, for example sodium hydride, according to Bull. Chem. Soc. Jap. 52, pp. 1735–1737 (1979).

Compounds of the formula I, in which one of the symbols $X_1$ and $X_2$ is unsubstituted amino, can be converted into corresponding compounds of formula I, wherein one of the symbols $X_1$ and $X_2$ is acylamino e.g. by reaction with activated carboxylic acid derivatives, such as acid halides, for example acid chlorides, for example in the presence of pyridine, according to J. Org. Chem. 40, pp. 526–527 (1975).

Furthermore, compounds of the formula I, in which one of the symbols $X_1$ and $X_2$ is unsubstituted or substituted amino and the other is free or functionally modified formyl, free or functionally modified carboxyl or acyl, can be converted into corresponding compounds of the formula I, in which one of the symbols $X_1$ and $X_2$ is hydroxy and the other is free or functionally modified formyl, free or functionally modified carboxyl or acyl, by hydrolysis, preferably with heating, for example in the presence or potassium carbonate.

Compounds of the formula I, in which one of the symbols $X_1$ and $X_2$ is disubstituted amino and the other is free or functionally modified formyl, free or functionally modified carboxyl or acyl, can be converted into corresponding compounds of the formula I, in which one of the symbols $X_1$ and $X_2$ is an unsubstituted or substituted hydrocarbon radical or heterocyclic radical and the other is free or functionally modified formyl, free or functionally modified carboxyl or acyl, e.g. by reaction with an organometal, especially organolithium derivative of a hydrocarbon or a heterocyclic compound, preferably a lower-alkyllithium reagent, such as n-butyllithium, e.g. in the presence of an ether, for example tetrahydrofuran, as a solvent, preferably under an inert gas atmosphere, such as nitrogen, according to J. Org. Chem. 43, pp. 4248–4250 (1978).

A further process variant consists of the use of an organomagnesium derivative, such as methylmagnesium iodide, instead of the organolithium derivative mentioned above according to Chem. Rev. 66, pp. 171–172 (1966).

Compounds of the formula I, in which one of the symbols $X_1$ and $X_2$ is unsubstituted or substituted amino and the other is free of functionally modified formyl, free or functionally modified carboxyl or acyl, can be converted into corresponding compounds of the formula I, in which one of the symbols $X_1$ and $X_2$ is free or etherified mercapto and the other is free or functionally modified formyl, free of functionally modified carboxyl or acyl, by reaction e.g. with sodium hydrogen-sulfide or with an alkyl- or arylmercaptane.

Compounds of the formula I, in which one of the symbols $X_1$ and $X_2$ is a quaternary ammonium salt and the other is free or functionally modified formyl, free or functionally modified carboxyl or acyl, can be converted into corresponding compounds of the formula I, in which one of the symbols $X_1$ and $X_2$ is nitro and the other is free or functionally modified formyl, free or functionally modified carboxyl or acyl, e.g. by reaction with sodium nitrite according to Chem. Rev. 66, 172 (1966).

Furthermore, compounds of the formula I, in which one of the symbols $X_1$ and $X_2$ is cyano and the other is free of functionally modified formyl, free or functionally modified carboxyl or acyl, can be obtained e.g.

from corresponding compounds of formula I, in which one of the symbols $X_1$ and $X_2$ is a quaternary ammonium salt and the other is free or functionally modified formyl, free or functionally modified carboxyl or acyl, by reaction e.g. with an alkalimetal cyanide, for example sodium cyanide, according to Chem. Rev. 66, p. 173 (1966).

Compounds of the formula I, in which one of the symbols $X_1$ and $X_2$ is a [2,2-di-(lower-alkoxycarbonyl)-vinyl] group, can be converted into corresponding compounds of the formula I, wherein one of the symbols $X_1$ and $X_2$ is carboxyethenyl by decarboxylation. The decarboxylation can be performed e.g. by pyrolysis or by hydrolysis, for example in an alkaline or acid medium.

Compounds of the formula I, wherein one of the symbols $X_1$ and $X_2$ is a α-hydroxy hydrocarbon radical and the other is halogen, can be oxidized e.g. with chromium(IV)oxide to corresponding compounds of formula I, wherein one of the symbols $X_1$ and $X_2$ is acyl and the other is halogen, according to Zh. Obshch. Khim. 34, 354 (1964).

As a process variant, it is also possible to oxidize compounds of the formula I, wherein one of the symbols $X_1$ and $X_2$ is a α-lower-alkoxy hydrocarbon radical and the other is halogen, to corresponding compounds of formula I, wherein one of the symbols $X_1$ and $X_2$ is acyl including formyl and the other is halogen, e.g. with N-bromosuccinimide preferably in an aprotic solvent, such as tetrachloromethane, according to Synthesis 1981, 484.

Compounds of the formula I, wherein one of the symbols $X_1$ and $X_2$ is free or esterified carboxyl and the other is halogen, can be reduced to corresponding compounds of the formula I, wherein one of the symbols $X_1$ and $H_2$ is hydroxymethyl and the other is halogen, e.g. by reaction with lithium aluminium hydride according to J. Amer. Chem. Soc. 102, 6519 (1980).

Compounds of the formula I, wherein one of the symbols $X_1$ and $X_2$ is a halogen-substituted hydrocarbon radical and the other is halogen, can be reduced to corresponding compounds of the formula I, wherein one of the symbols $X_1$ and $X_2$ is a hydrocarbon radical and the other is halogen, e.g. by reaction with lithium aluminium hydride according to J. Amer. Chem. Soc. 102, 6519 (1980).

Compounds of the formula I, wherein one of the symbols $X_1$ and $X_2$ is a free or metallised mercapto, can be converted into corresponding compounds of the formula I, wherein one of the symbols $X_1$ and $X_2$ is etherified mercapto, e.g. by reaction with a hydrocarbon or heterocyclic compound bearing a halogen radical, for example a chlorine radical, such as a compound of the formula II, for example 4-chloro-3-formylflav-3-ene.

Furthermore, it is possible within the scope of the definition of the compounds of the formula I to convert compounds obtained in customary manner into other compounds of the formula I by modifying, introducing or splitting off suitable substituents.

Free carboxy groups can be esterified in customary manner, for example by reacting with a corresponding alcohol, advantageously in the presence of an acid, such as a mineral acid, for example sulfuric acid or hydrochloric acid, or in the presence of a water-binding agent, such as dicyclohexylcarbodiimide, or by reacting with a corresponding diazo compound, for example diazomethane. Esterification can also be carried out by reacting a salt, preferably an alkali metal salt, of the acid with a reactive esterified alcohol, for example a corresponding halide, such as a chloride.

Free carboxy groups can be amidated in customary manner, for example by reacting with ammonia or with a primary or secondary amine, advantageously in the presence of a water-binding agent, such as dicyclohexylcarbodiimide, or by converting the carboxy group into a halocarbonyl group, for example a chlorocarbonyl group, and then reacting with ammonia or a primary or secondary amine.

In compounds that contain an esterified carboxyl group, the latter can be converted into a free carboxy group in customary manner, for example by hydrolysis, preferably in the presence of strong bases, such as an alkali metal hydroxide, for example sodium or potassium hydroxide, or strong acids, for example a strong mineral acid, such as a hydrohalic acid, for example hydrochloric acid, or sulfuric acid.

In compounds having an esterified carboxyl group as substituent, the latter can be converted into the corresponding carbamoyl group in customary manner, for example by ammonolysis or aminolysis with ammonia or a primary or secondary amine.

Compounds having a carbamoyl group as substituent can be dehydrated to form the corresponding cyano compounds in customary manner, for example by the action of dehydrating agents, such as phosphorus pentoxide, phosphorous oxychloride or trifluoroacetic acid anhydride, preferably at elevated temperatures.

In compounds having an esterified carboxyl group as substituent, the esterified carboxyl group can be converted into a cyano group in customary manner, for example by the action of an organic aluminium amide compound, such as a di-lower alkylaluminium amide compound, for example diethylaluminium amide.

Compounds containing a cyano substituent can be hydrolysed to the corresponding carbamoyl compounds or directly to the carboxy compounds in customary manner, for example in the presence of concentrated aqueous mineral acids or alkali metal hydroxides.

Compounds having a cyano group as substituent can be alcoholysed to form corresponding compounds having esterified carboxyl groups in customary manner, for example by the addition of alcohols in the presence of an anhydrous acid, such a hydrogen chloride, and subsequent hydrolysis of the resulting imido ester.

Compounds of the formula I containing a primary or secondary amino group as substituent can be converted into compounds of the formula I which contain a tertiary amino group by introducing a substituent, for example an optionally substituted lower alkyl group, such as methyl or benzyl, in customary manner, for example using a corresponding reactive esterified alcohol, such as a corresponding halide, for example chloride or bromide, or a diazoalkane, for example diazomethane.

Compounds that carry a lower alkylthio group, for example a methylthio group, can be converted into the sulfur-free compounds by treating with suitable desulfurating agents, for example Raney nickel, in a suitable solvent, for example dioxane.

In compounds which carry at least one aromatic hydroxy group as substituent, this may be etherified in customary manner. The reaction to form the corresponding ethers is carried out, for example, in the presence of bases, such as alkali metal hydroxides or carbonates, for example sodium hydroxide or potassium carbonate, by means of di-lower-alkylsulfuates or lower alkyl halides or in the presence of a dehydrating agent, for example dicyclohexylcarbodiimide, by means of lower alkanols.

In compounds in which an aliphatically or cycloaliphatically bonded hydroxy or mercapto group is present, for example as substituent of the rings A and/or B, this group may be etherified in customary manner. Suitable etherifying agents are e.g. diazo compounds, such as unsubstituted or substituted diazo-lower alkanes, for example diazomethane. Further suitable etherifying agents are esters of corresponding alcohols, especially those with strong inorganic or organic acids, such as mineral acids, e.g. hydrohalic acids, such as hydrochloric acid, and also sulfuric acid, or strong sulfonic acids, such as lower alkanesulfonic acids which are unsubstituted or substituted e.g. by lower alkyl, such as methyl, for example methanesulfonic acid, trifluoromethanesulfonic acid or p-toluenesulfonic acid. Such esters are for example lower alkyl halides, for examples methyl iodide, or sulfates, such as dimethyl sulfate.

Compounds of the formula I containing at least one esterified hydroxy and/or mercapto group as substituent or as a value of $X_1$ or $X_2$ can be obtained by treating a compound of the formula I, in which at least one hydroxy and/or mercapto group is present as substituent or as a value of $X_1$ and $X_2$, with an acylating agent introducing the desired acyl radical. Such agents are, for example, optionally substituted lower alkanecarboxylic or lower alkanesulfonic acids, optionally substituted benzoic or phenylsulfonic acids or reactive derivatives thereof, such as anhydrides or acid halides, for example acid chlorides, e.g. acetyl chloride, methylsulfonyl chloride, benzoyl chloride or p-tolylsulfonyl chloride, or hydrohalic acids, especially in the form of reactive esters, for example thionylchloride and phosphorous tribromide.

Conversely, compounds of the formula I in which at least one esterified hydroxy and/or mercapto group is present as substituent can be converted into compounds of the formula I containing at least one hydroxy and/or mercapto group. The conversion to hydroxy and/or mercapto is carried out, for example, by alcoholysis with a lower alkanol, for example methanol or ethanol, or preferably by hydrolysis, such as base-catalysed hydrolysis, for example in the presence of sodium hydroxide.

Lower alkoxy and phenoxy groups as well as lower alkylthio and phenylthio groups can be converted to free hydroxy and free mercapto groups e.g. by mineral acids, such as hydrohalic acids, e.g. hydroiodic acid, or Lewis acids, for example aluminium trichloride.

As in the manufacturing processes, when carrying out the additional steps, care must be taken that undesired side reactions which may result in the conversion of additional groupings do not occur.

The reactions described above may be carried out simultaneously or in succession, as desired, and also in any sequence. If necessary, they are carried out in the presence of diluents, condensation agents and/or catalytically active agents, at reduced or elevated temperature, in a closed vessel under pressure and/or in an inert gas atmosphere.

Acid addition salts of compounds of the formula I are obtained in customary manner, for example by treating with an acid or a suitable anion exchanger. The resulting salts can be converted into the free compounds in a manner known per se, for example by treating with a suitable basic agent, for example a metal hydroxide, ammonia or a hydroxyl ion exchanger. On the other hand, compounds having an acidic group, e.g. a carboxy or a phenolic hydroxy group, can be converted into an alkali metal salt in a manner known per se by treating, for example, with an alkali metal hydroxide. The free compounds can be obtained by treating with an acid.

Salts of compounds of the formula I are especially pharmaceutically acceptable non-toxic salts, such as those of compounds of the formula I with acidic groups, for example with a free carboxyl or sulfo group. Such salts are especially metal or ammonium salts, such as alkali metal or alkaline earth metal salts, for example sodium, potassium, magnesium or calcium salts, as well as ammonium salts, which are formed with ammonia or suitable organic amines. There come into consideration for the salt formation especially aliphatic, cycloaliphatic, cycloaliphatic-aliphatic or araliphatic primary, secondary or tertiary mono-, di- or poly-amines, as well as heterocyclic cyclic bases, such as lower alkylamines, for example di- or tri-ethylamine, hydroxy-lower alkylamines, for example 2-hydroxyethylamine, bis-(2-hydroxyethyl)-amine or tris-(2-hydroxyethyl)-amine, basic aliphatic esters or carboxylic acids, for example 4-aminobenzoic acid, 2-diethylaminoethyl ester, lower alkyleneamines, for example 1-ethylpiperidine, cycloalkylamines, for example dicyclohexylamine, or benzylamines, for example, N,N'-dibenzylethylenediamine.

Compounds of the formula I having a basic group may form acid addition salts, for example with inorganic acids, such as hydrochloric acid, sulfuric acid or phosphoric acid, or with suitable organic carboxylic or sulfonic acids, for example acetic acid, succinic acid, fumaric acid, tartaric acid, methanesulfonic acid and p-toluenesulfonic acid. In the presence of several acidic or basic groups, mono- or poly-salts may be formed. Compounds of the formula I having an acidic group, for example a free carboxy group, and a basic group, for example an amino group, may also be present in the form of inner salts, i.e., in zwitterionic form, or a part of the molecule may be present in the form of an inner salt and another part in the form of a normal salt.

The pharmaceutically acceptable salts mentioned hereinbefore are preferred. For isolation or purification it is also possible to use other salts than the therapeutically acceptable salts. Owing to the close relationships between the novel compounds in free form and in the form of their salts, hereinbefore and hereinafter there shall optionally be understood by free compounds and salts, where appropriate with regard to meaning and purpose, also the corresponding salts and free compounds, respectively.

The compounds of the formula I, including their salts, can also be obtained in the form of their hydrates or can include the solvent used for their crystallisation.

The compounds of the formula I have at least one asymmetric center at the carbon atom 2. Therefore they can be found as R- or S-enantiomers as well as a racemate. The present invention is intended to include all these forms, also those further stereoisomers, and mixtures of at least two stereoisomers, for example a diastereomeric mixture or enantiomeric mixture, such as a racemate, which are possible if one or more other asymmetric centers are present within the molecule.

Starting materials and end products that are isomeric mixtures can be separated into the individual isomers by methods known per se, for example by fractional distillation, crystallisation and/or chromatography. Racemic products can be separated into the optical antipodes, for example by chromatography and/or separation of their diastereoisomeric salts, for example by fractional crystallisation of the d- or l-camphor-sulfonates, -mandelates, -tartrates or -dibenzoyltartrates.

The invention relates also to modifications of the present process, according to which an intermediate obtainable at any stage of the process is used as starting material and the remaining process steps are carried out, or the process is discontinued at any stage, or according to which a starting material is formed under the reaction conditions, or in which a starting material is used in the form of a salt or a reactive derivative. The invention also comprises novel intermediates resulting therefrom.

In the process of the present invention the starting materials used are preferably those which result in the compounds described at the beginning as being especially valuable.

The starting materials used in the process for the manufacture of the compounds of the present invention are known or, if they are novel, they can be manufactured by methods known per se, for example in a manner analogous to that described in the Examples. The invention relates also to novel starting materials.

The pharmaceutical preparations according to the invention contain at least one compound of the general formula I or a salt thereof as the active substance together with a customary pharmaceutical carrier. The type of carrier depends largely on the field of use. The pharmaceutical compositions according to the invention which contain, as active substances, compounds of the formula I can be administered enterally, such as orally or rectally, parenterally, e.g. subcutaneously, intramuscularly or intravenously, or by inhalation.

For oral treatment, especially solid dosage unit forms, such as tablets, dragees and capsules are considered, which preferably contain between 10 and 90% of an active substance of the general formula I or a salt in order to allow administration to warm-blooded animals of daily doses of from 0.1 to 100 mg/kg, especially from 1 to 50 mg/kg. The daily doses depends on age and individual condition and also on the mode of administration. For the manufacture of tablets and dragee cores, the compounds of the general formula I are combined with solid, pulverulent carriers, such as lactose, saccharose, sorbitol, maize starch, potato starch or amyl opectin, cellulose derivatives or gelatine, preferably with the addition of lubricants, such as magnesium or calcium stearate, or polyethylene glycols of a suitable molecular weight. Dragee cores are subsequently coated, for example with concentrated sugar solutions which may contain, in addition, gum arabic, talc and/or titanium dioxide, or with a lacquer dissolved in readily volatile organic solvents or solvent mixtures. Colouring substances can be added to these coatings, for example for indicating different doses of active substance. Soft gelatine capsules and other closed capsules consist, for example, of a mixture of gelatine and glycerin and may contain, for example, mixtures of a compound of the formula I and polyethylene glycol. Dry-filled capsules contain, for example, granules of an active substance with solid, pulverulent carriers, such as, for example, lactose, saccharose, sorbitol, mannitol; starches, such as potato starch, maize strach or amylopectin, cellulose derivatives and gelatine and also magnesium stearate or stearic acid.

Unit dosage forms that come into consideration for rectal administration are, for example, suppositories which consist of a combination of an active substance with a suppository base based on natural or synthetic triglycerides (for example cocoa butter), polyethylene glycols or suitable higher fatty alcohols, and gelatine rectal capsules which contain a combination of the active substance with polyethylene glycols.

Ampoule solutions for parenteral administration, especially for intramuscular or intravenous administration, contain a compound of the formula I or a salt thereof in a concentration of preferably 0.5 to 5% as an aqueous dispersion prepared with the aid of customary solubilisers and/or emulsifiers, and, optionally, stabilisers, or preferably as an aqueous solution of a pharmaceutically acceptable water-soluble salt of a compound of the general formula I.

For inhalation the active compound may be presented in association with volatile excipients, as a cream, lotion, paste or ointment or as a finely divided dry power or in solution for inhalation through a nasal spray, atomiser or insufflator.

Inhalation preparations for the treatment of the respirator tract by nasal, buccal or intrapulmonary administration are e.g. aerosols or sprays that can disperse the pharmacological active ingredient in the form of a powder or in the form of drops of a solution or suspension. Preparations having powder-dispersing properties generally contain, apart from the active ingredient, a liquid propellant gas having a boiling point of below room temperature and, if desired, carriers, such as liquid or solid, non-ionic or anionic surface-active agents and/or solid diluents. Preparations in which the pharmacological active ingredient is in solution, contain, in addition, a suitable propellant, and also, if necessary, an additional solvent and/or a stabiliser. Instead of the propellant gas, it is also possible to use compressed air, and this can be produced as required by means of a suitable compression and release device.

The concentration of the active substance for liquids that are to be taken orally, such as syrups or elixirs, is so selected that a single dose can easily be measured, for example as the contents of a teaspoon or a measuring spoon of, for example, 5 ml, or also as a multiple of that volume.

The following Examples (a) to (c) are intended to illustrate the manufacture of some typical forms of administration, but do not in any way represent the only embodiments of those forms of administration.

(a) 250 g of active substance are mixed with 550 g of lactose and 292 g of potato starch, and the mixture is moistened with an alcoholic solution of 8 g of gelatine and granulated by being passed through a sieve. After drying, 60 g of talc, 10 g of magnesium stearate and 20 g of colloidal silica are added and the mixture is pressed to form 10,000 tablets each weighing 119 mg and each containing 25 mg of active substance, which may, if desired, be provided with dividing notches of a finer adjustment of the dosage.

(b) A granulate is prepared from 100 g of active substance, 379 g of lactose and the alcoholic solution of 6 g of gelatine, which, after being dried, is mixed with 10 g of colloidal silica, 40 g of talc, 60 g of potato starch and 5 g of magnesium stearate and pressed to form 10,000 dragee cores. These are subsequently coated with a concentrated syrup consisting of 533.5 g of cryst, saccharose, 20 g of shellac, 75 g of gum arabic, 250 g of talc, 20 g of colloidal silica and 1.5 g of colouring substance, and dried. The resulting dragees each weight 150 mg and each contain 10 mg of active substance.

(c) 25 g of active substance and 1975 g of finely ground suppository base (for example, cocoa butter) are thoroughly mixed and then melted. 1000 suppositories of 2 g are cast from the melt which has been kept homogenous by stirring. They each contain 25 mg of active substance.

The following Examples serve to illustrate the invention but are not intended to limit the scope thereof in any way. Temperatures are given in degrees Centigrade. Unless defined otherwise, the evaporation of solvents is carried out under reduced pressure, for example between approximately 0.1 and 20 mbar.

EXAMPLE 1

0.14 g sodium is allowed to react with 15 ml absolute methanol. After complete disappearance of sodium, one adds 1.35 g 4-chloro-3-formyl-flav-3-ene. After 2 hours stirring at room temperature, 5 ml water is added, the solution concentrated and extracted with methylene chloride. The organic phase is evaporated and the residual solid is crystallized in a mixture of acetone and hexane. Pure 3-formyl-4-methoxy-flav-3-ene is obtained as yellow crystals, m.p. 68°–70° C.

EXAMPLE 2

1.7 g sodium is allowed to react with 150 ml absolute ethanol. After complete disappearance of sodium, one adds 13.5 g 4-chloro-3-formyl-flav-3-ene. After stirring 30 minutes at 40° C., 300 ml of water is added and a precipitate is formed, filtered, washed with water and dried. The solid is crystallized in hexane. Pure 4-ethoxy-3-formyl-flav-3-ene is obtained as yellow crystals; m.p. 80°–82° C.

EXAMPLE 3

A solution of 5 g 4-chloro-3-formyl-flav-3-ene in 100 ml diethylether is refluxed. To this solution one adds 7.3 ml piperidine. After 4 days reflux, the precipitate is filtered and washed with ether. The precipitate is dissolved in methylene chloride and this organic phase is washed with water and dried over magnesium sulfate. After evaporation the residue is crystallized in diisopropylether. Pure 3-formyl-4-(N-piperidino)-flav-3-ene is obtained as yellow crystals; m.p. 189°–190° C.

EXAMPLE 4

A solution of 0.27 g 4-chloro-3-formyl-flav-3-ene and 0.1 g morpholine in 3 ml methylene chloride is refluxed over night. After cooling and neutralization with a 1N hydrochloric acid solution the mixture is extracted with methylene chloride. After evaporation the crude solid is crystallized in toluene. Pure 3-formyl-4-(N-morpholino)flav-3-ene is obtained as yellow brown crystals; m.p. 227°–229° C.

EXAMPLE 5

A solution of 0.27 g 4-chloro-3-formyl-flav-3-ene and 0.1 ml thiomorpholine in 3 ml methylene chloride is refluxed over night. After cooling and neutralization with a 1N hydrochloric acid solution. the mixture is extracted with methylene chloride. After evaporation the crude solid is crystallized in ethanol. Pure 3-formyl-4-(N-thiomorpholino)-flav-3-ene is obtained as yellow brown crystals; m.p. 178°–180° C.

EXAMPLE 6

1.25 g sodium is allowed to react with 150 ml absolute methanol. When all the sodium has disappeared, one adds 6 ml benzylmercaptan and 13.5 g 4-chloro-3-formyl-flav-3-ene and refluxes over 15 minutes. After solvent evaporation and extraction with methylene chloride the residue is crystallized in a mixture of hexane and diisopropylether. Pure 4-benzylmercapto-3-formyl-flav-3-ene is obtained as yellow crystals; m.p. 99°–100° C.

EXAMPLE 7

A mixture of 26 g 4-chloro-3-formyl-flav-3-ene and 7.1 g sodium hydrosulfide hydrate in 400 ml ethanol is refluxed for 3 hours and allowed to stand overnight at room temperature. The reaction mixture is evaporated to dryness and the residue dissolved in methylene chloride. The precipitate is filtered and the organic solution is evaporated. The residue is recrystallized in a mixture of hexane and toluene. Pure 4-(2″H-3″-formyl-2″-phenyl-1″-benzopyran-4″-yl-thio)-3-formyl-flav-3-ene is obtained as yellow crystals; m.p. 193°–194° C.

EXAMPLE 8

2.88 g magnesium is allowed to react with 16.82 g methyl iodide in 80 ml refluxing dry diethylether. After disappearance of magnesium, one adds a solution of 21.4 g 4-chloro-3-formyl-flav-3-ene in 100 ml of a mixture of diethylether and tetrahydrofuran. After cooling to 0° C., a solution of 12.68 g ammonium chloride in 160 ml water is added. The two phases are separated and the aqueous solution is extracted with 50 ml diethyl ether. The combined organic phases are washed with 50 ml water, dried over magnesium sulfate and evaporated. The crude solid is crystallized in hexane. A racemate of one diastereomer of 4-chloro-3-(α-hydroxyethyl)-flav-3-ene is obtained as yellow crystals; m.p. 111°–113° C.

EXAMPLE 9

As in example 8 but after crystallization in hexane the mother liquor is purified by column chromatography on silica gel using a mixture of hexane and dichloromethane as eluant. After separation a racemic form of the other diastereomer of example 8, i.e. 4-chloro-3-(α-hydroxyethyl)-flav-3-ene is obtained as a yellow oil; $^1$H-NMR (100 MHz, CDCl$_3$): δ (ppm) 2.12 (1H, s, H—O—).

EXAMPLE 10

A solution of 27 g 4-chloro-3-formyl-flav-3-ene in 25 ml dimethylformamide is refluxed. To this solution one adds 7.7 g hydroxylamine hydrochloride dissolved in 60 ml dimethylformamide. After two hours reflux, the solution is cooled at room temperature before the addition of 400 ml water. The precipitate is formed, filtered, washed with water and dried. The solid is crystallized in diisopropylether. Pure 4-chloro-3-hydroxyiminomethyl-flav-3-ene is obtained as pale yellow crystals; m.p. 199°–200° C.

EXAMPLE 11

A solution of 25.7 g 4-chloro-3-hydroxyiminomethyl-flav-3-ene and 28.3 g triphenylphosphine in 250 ml 1,2-dichloroethane and 8.7 ml carbon tetrachloride is heated at 60° C. To this solution one adds 12.54 ml triethylamine. The temperature is maintained between 62°–65° C. during the addition and for further 25 minutes. The mixture is cooled to 0° C., filtered and evaporated. The crude material is extracted with hexane. The combined extracts are evaporated and purified by column chromatography on silicagel using a mixture of dichloromethane and hexane as eluant. The pure fraction is evaporated and crystallized in diisopropylether. Pure 4-chloro-3-cyano-flav-3-ene is obtained as pale yellow crystalls; m.p. 99° C.

EXAMPLE 12

A solution of 1.0 g 4-chloro-3-formyl-flav-3-ene and 0.68 g sarcosin ethyl ester hydrochloride in 10 ml pyridine is cooled at 10°–15° C. One adds 0.97 g triethylamine and warms at 55° C. for 60 hours. After cooling to 2° C., 0.74 ml 50% potassium hydroxide solution is added. After 10 minutes, one adds 37 ml water. The mixture is extracted with dichloromethane, dried over magnesium sulfate and evaporated. The residue is purified by column chromatography on silica gel using dichloromethane as eluant. The solid is crystallized in dichloromethane. Pure 3-formyl-4-(N-methyl-N-ethoxycarbonylmethylamino)flav-3-ene is obtained as yellow crystals; m.p. 158°–159° C.

EXAMPLE 13

To a stirred solution of 5.8 g 4-chloro-3-formyl-flav-3-ene in 500 ml tert-butanol and 100 ml 2-methylbut-2-ene at room temperature is added dropwise a solution of 17.9 g sodium chlorite and 17.9 g sodium dihydrogenophosphate in 200 ml water. Stirring is continued for 5 hours. The solution is concentrated in vacuo and water is added to the residue to give a suspension. The mixture is extracted with hexane and the clear organic extracts are discarded. Subsequently, the aqueous suspension is acidified to pH 3 and the mixture is extracted with chloroform. The combined chloroform extracts are washed with water, dried over magnesium sulfate, filtered and evaporated. The residual solid is recrystallized in a mixture of chloroform and hexane. Pure 4-chloro-3-carboxy-flav-3-ene is obtained as yellow crystals; m.p. 210° C.

EXAMPLE 14

To a stirred solution of 16 g 4-chloro-3-formyl-flav-3-ene in 500 ml dry methanol at room temperature is added 0.5 g sodium borohydride in small portions. After the addition is completed 500 ml water is added. The solution is filtered and extracted with chloroform. The combined organic extracts are dried over magnesium sulfate and evaporated. Chromatographically pure 4-chloro-3-hydroxymethyl-flav-3-ene is obtained as a yellowish oil; TLC (SiO$_2$, CHCl$_3$): 1 spot, R$_F$ 0.18.

EXAMPLE 15

To a stirred solution of 20 g 3-fromyl-flav-3-ene, obtained according to Eur. J. Med. Chem., Chim. Ther. 10, 72 (1975), and 120 g silver nitrate in 1.5 ml 96% ethanol and 400 ml water at room temperature, is added a solution of 40 g sodium hydroxide in 60 ml water. Stirring is continued for 3 hours. After filtration the yellow filtrate is acidified to pH 3. The precipitate which appears is collected and dried. This material is dissolved in a mixture of chloroform and water with stirring and heating. The organic phase is separated and dried over magnesium sulfate. After filtration, the solution is allowed to stand at 4° C. for one day. The powder which has precipitated is filtered. Pure 3-carboxy-flav-3-ene is obtained as pale yellow crystals; m.p. 230° C.

EXAMPLE 16

A solution containing 2.7 g 4-chloro-3-formyl-flav-3-ene, 0.85 ml thioglycolic acid and 2.5 g sodium bicarbonate in 30 ml absolute ethanol is refluxed for 15 hours. After evaporation, one adds water and extracts with methylene chloride. The aqueous phase is acidified to pH 1. Extraction with methylene chloride is followed by washing the organic solution with water, drying over magnesium sulfate and evaporation. The residue is purified by column chromatography on silicagel using a mixture of methylene chloride and ethanol as eluant. The best fractions are crystallized in a mixture of hexane and toluene. Pure 4-(S-carboxymethylthio)-3-formyl-flav-3-ene is obtained as yellow crystals; m.p. 127°–129° C.

EXAMPLE 17

A solution of 81 g 4-chloro-3-formyl-flav-3-ene and 80 ml dimethylamine in 810 ml tetrahydrofurane is stirred at room temperature for one hour. After cooling to 0° C. the precipitate is filtered. This precipitate is washed with tetrahydrofurane, then dissolved in methylene chloride, washed with water, dried over magnesium sulfate and evaporated. The crude solid is recrystallized in toluene. Pure 4-N,N-dimethylamino-3-formyl-flav-3-ene is obtained as yellow crystals; m.p. 182°–187° C.

EXAMPLE 18

A solution of 0.48 g 4-methoxy-flav-3-ene, 1 ml trifluoroacetic anhydride and 0.2 ml pyridine in 9 ml methylene chloride is stirred at room temperature for one hour. After washing with water, drying over magnesium sulfate and evaporation, the crude solid is recrystallized from hexane. Pure 4-methoxy-3-trifluoroacetyl-flav-3-ene is obtained as yellow crystals, m.p. 88°–90° C.

EXAMPLE 19

As in example 14 but starting from 3.16 g 4-chloro-3-formyl-8-methoxy-thioflav-3-ene in 30 ml dry methanol and 0.35 g sodium borohydride. After work up, the crude oil is crystallized in a mixture of n-hexane and ethylacetate. Pure 4-chloro-3-hydroxymethyl-8-methoxy-thioflav-3-ene is obtained as yellow crystals; m.p. 143°–145° C.-TLC (SiO$_2$, n-hexane CH$_2$Cl$_2$ 1:1): R$_f$=0.05.

EXAMPLE 20

As in example 13 but starting from 3.16 g of 4-chloro-3-formyl-8-methoxy-thioflav-3-ene, 250 ml tert-butanol and 60 ml 2-methyl-2-butene. After work up the crude oil is crystallised in a mixture of n-hexane and ethyl acetate. Pure 3-carboxy-4-chloro-8-methoxy-thioflav-3-ene is obtained as yellow crystals; m.p. 207°–210° C.-TLC (SiO$_2$, CH$_2$Cl$_2$/Acetone/HCOOH 18/1/1): R$_f$=0.45.

EXAMPLE 21

As in example 11 but starting with 1 g 4-chloro-3-hydroxyiminomethyl-8-methoxy-thioflav-3-ene. The crude material is extracted with CH$_2$Cl$_2$. The combined extracts are evaporated and purified by column chromatography on silicagel using a mixture of n-hexane and acetone as eluant. Pure 4-chloro-3-cyano-8-methoxy-thioflav-3-ene is obtained as a yellow solid. TLC (SiO$_2$, n-hexane/acetone 4:1): R$_f$=0.25.-NMR (90 MHz, CDCl$_3$): δ(ppm)=3.81 [s, 3H, OCH$_3$], 4.9 [s, 1H, H-

C(2)], 7.3 [s, 5H, H-C(2',3',4',5',6')], 6.75–7.76 [m, 3H, H-C(5,6,7)].-M.p. 134°–140° C.(ligroin).

EXAMPLE 22

As in example 10 but starting with 1 g 4-chloro-3-formyl-8-methoxy-thioflav-3-ene in 1.5 ml DMF. 220 mg hydroxylamine hydrochloride dissolved in 2 ml DMF are added. After 1½ hours of reflux, the solution is cooled at room temperature before the addition of 20 ml of water. After extraction with $CH_2Cl_2$ a gum is obtained which is purified by column chromatography on silicagel using n-hexane/acetone 9:1 as eluant. Pure 4-chloro-3-hydroxyiminomethyl-8-methoxy-thioflav-3-ene is obtained as a yellow solid. TLC ($SiO_2$, n-hexane/acetone 4:1): $R_f$=0.15.-NMR (90 MHz, $CDCl_3$): $\delta(ppm)$=3.76 (s, 3H, $OCH_3$), 5.5 [s, 1H, H-C(2)], 6.76–7.69 [m, 3H, H-C(5,6,7)], 7.17 [s, 5H, H-C(2',3',4',5',6')], 8.53 [s, 1H, CH=N], 11.4 [s, 1H, OH].-M.p. 190°–203° C. (n-hexane/toluene).

EXAMPLE 23

As in example 14 but starting from 16 g 3-chloro-4-formyl-flav-3-ene. Pure 3-chloro-4-hydroxymethyl-flav-3-ene is obtained as a white solid. TLC ($SiO_2$, cyclohexane/diisopropyl ether 1:1): $R_f$=0.4.-NMR (90 MHz, $CDCl_3$). $\delta(ppm)$=2.02 (1H, s, OH), 4.73 (2H, s, $CH_2OH$), 5.79 [1H, s, H-C(2)], 6.7–8 (9H, m, aryl-H).

EXAMPLE 24

As in example 13, but starting from 5.8 g 3-chloro-4-formyl-flav-3-ene. Pure 4-carboxy-3-chloro-flav-3-ene is obtained as a white solid. TLC ($SiO_2$, $CH_2Cl_2$/acetone/HCOOH 18:1:1): $R_f$=0.55.-NMR (90 MHz, DMSO-$d_6$): $\delta(ppm)$=6.11 [1H, s, H-C(2)], 6.75–7.56 [4H, m, H-C(5,6,7,8)], 7.41 (5H, s, $C_6H_5$).

EXAMPLE 25

Following the procedure as described in example 1 but starting from 3-chloro-4-formyl-flav-3-ene, results in pure 4-formyl-3-methoxy-flav-3-ene.

EXAMPLE 26

Following the procedure as described in example 2 but starting from 3-chloro-4-formyl-flav-3-ene, results in pure 3-ethoxy-4-formyl-flav-3-ene.

EXAMPLE 27

Following the procedure as described in example 3 but starting from 3-chloro-4-formyl-flav-3-ene, results in pure 4-formyl-3-(N-piperidino)-flav-3-ene.

EXAMPLE 28

Following the procedure as described in example 4 but starting from 3-chloro-4-formyl-flav-3-ene, results in pure 4-formyl-3-(N-morpholino)-flav-3-ene.

EXAMPLE 29

Following the procedure as described in example 5 but starting from 3-chloro-4-formyl-flav-3-ene, results in pure 4-formyl-3-(N-thiomorpholino)-flav-3-ene.

EXAMPLE 30

Following the procedure as described in example 6 but starting from 3-chloro-4-formyl-flav-3-ene, results in pure 3-benzylmercapto-4-formyl-flav-3-ene.

EXAMPLE 31

Following the procedure as described in example 8, but starting from 3-chloro-4-formyl-flav-3-ene, results in pure 3-chloro-4-(α-hydroxyethyl)-flav-3-ene.

EXAMPLE 32

Following the procedure as described in example 10 but starting from 3-chloro-4-formyl-flav-3-ene, results in pure 3-chloro-4-hydroxyiminomethyl-flav-3-ene.

EXAMPLE 33

Following the procedure as described in example 11 but starting from 3-chloro-4-hydroxyiminomethyl-flav-3-ene, results in pure 3-chloro-4-cyano-flav-3-ene.

EXAMPLE 34

Following the procedure as described in example 16 but starting from 3-chloro-4-formyl-flav-3-ene, results in pure 3-(S-carboxymethylthio)-4-formyl-flav-3-ene.

EXAMPLE 35

Following the procedure as described in example 17 but starting from 3-chloro-4-formyl-flav-3-ene, results in pure 3-N,N-dimethylamino-4-formyl-flav-3-ene.

We claim:
1. A compound of the formula

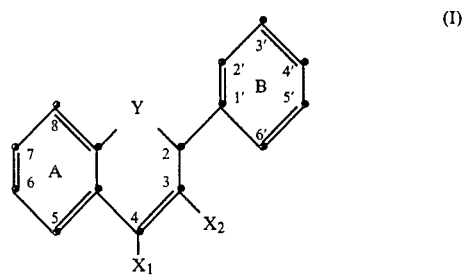

(I)

wherein one of the radicals $X_1$ and $X_2$ is selected from the group (a) consisting of formyl; imino lower alkyl which is unsubstituted or substituted by hydroxy or phenyl; carboxy; cyano; lower alkylcarbonyl which is unsubstituted or substituted by halogen; lower alkyl which is unsubstituted or substituted by hydroxy;

the other of $X_1$ and $X_2$ is selected from the group (b) consisting of hydrogen; halogen; amino; lower alkyl amino or di-lower alkyl amino, the lower alkyl portion thereof being unsubstituted or substituted by carboxy or lower alkoxycarbonyl; lower alkylene amino; aza-lower alkylene amino; oxa-lower alkylene amino; thia lower alkylene amino; phenylamino; lower alkoxy; lower alkylthio which is unsubstituted or substituted by carboxy or lower alkoxycarbonyl; benzylthio; and 2H-3-formyl-2-phenyl-1-benzopyran-4-yl-thio;

Y is oxygen or sulfur, but must be sulfur if $X_1$ is hydrogen and $X_2$ is formyl or lower alkyl;

and rings A and B are independently unsubstituted or substituted by a substituent selected from lower alkyl, lower alkoxy, halogen and nitro;

provided that $X_1$ and $X_2$ cannot be together halogen and formyl; or a pharmaceutically acceptable salt thereof.

2. The compound of claim 1 wherein one of $X_1$ and $X_2$ is selected from the group consisting of formyl; carboxy; cyano; halogeno lower alkyl carbonyl; hydroxy lower alkyl; and hydroxy imino lower alkyl; the other of $X_1$ and $X_2$ being selected from the group consisting of hydrogen, halogen, di-lower alkyl amino; N-lower alkyl-N-lower alkoxy carbonyl lower alkyl amino; N-piperidino; N-morpholino; N-thiomorpholino; lower alkoxy; carboxy lower alkyl thio; benzylthio; and 2H-3-formyl-2-phenyl-1-benzopyran-4-yl-thio; and wherein ring B is unsubstituted and ring A is unsubstituted or substituted at position 8 by lower alkoxy.

3. The compound of claim 2 which is selected from 3-formyl-4-methoxy-flav-3-ene; 4-ethoxy-3-formyl-flav-3-ene; 3-formyl-4-(N-piperidino)-flav-3-ene; 3-formyl-4-(N-morpholino)-flav-3-ene; 3-formyl-4-(N-thiomorpholino)-flav-3-ene; 3-benzylmercapto-3-formyl-flav-3-ene; 4-(2″H-3″-formyl-2″-phenyl-1″-benzopyran-4‴-yl-thio)-3-formyl-flav-3-ene; 4-chloro-3-(alphahydroxyethyl)-flav-3-ene; 4-chloro-3-hydroxyiminomethyl-flav-3-ene; 4-chloro-3-cyano-flav-3-ene; 3-formyl-4-(N-methyl-N-ethoxycarbonylmethylamino)-flav-3-ene; 4-chloro-3-carboxy-flav-3-ene; 4-chloro-3-hydroxymethyl-flav-3-ene; 3-carboxy-flav-3-ene; 4-(S-carboxymethylthio)-3-formyl-flav-3-ene; 4-N,N-dimethylamino-3-formyl-flav-3-ene; 4-methoxy-3-trifluoroacetyl-flav-3-ene; 4-chloro-3-hydroxymethyl-8-methoxy-thioflav-3-ene; 3-carboxy-4-chloro-8-methoxy-thioflav-3-ene; 4-chloro-3-cyano-8-methoxy-thioflav-3-ene; 4-chloro-3-hydroxyiminomethyl-8-methoxy-thioflav-3-ene; 3-chloro-4-hydroxymethyl-flav-3-ene; 4-carboxy-3-chloro-flav-3-ene; 3-methoxy-4-formyl-flav-3-ene; 3-ethoxy-4-formyl-flav-3-ene; 4-formyl-3-(N-piperidino)-flav-3-ene; 4-formyl-3-(N-morpholino)flav-3-ene; 3-benzylmercapto-4-formyl-flav-3-ene; 3-chloro-4-(alpha-hydroxyethyl)-flav-3-ene; 3-chloro-4-hydroxyiminomethylflav-3-ene; 3-chloro-4-cyano-flav-3-ene; 3-(S-carboxymethylthio)-4-formyl-flav-3-ene; 4-formyl-3-(N-thiomorpholino)-flav-3-ene; and 3-N,N-dimethylamino-4-formyl-flav-3-ene.

4. A compound of claim 1 wherein the radical $X_1$ is a member selected from said (a) which is bound via a non-carbon atom of said (a) moiety and radical $X_2$ is a member selected from said (b) which is bound via a carbon atom of said (b) moiety.

5. The compound of claim 1 which is 3-formyl-4-ethoxy-flav-3-ene.

6. The compound of claim 1 which is 3-formyl-4-methoxy-flav-3-ene.

* * * * *